(12) United States Patent
Bossenmaier et al.

(10) Patent No.: US 8,883,159 B2
(45) Date of Patent: Nov. 11, 2014

(54) ANTIBODIES AGAINST CDCP1 FOR THE TREATMENT OF CANCER

(75) Inventors: Birgit Bossenmaier, Seefeld (DE);
Georg Fertig, Penzberg (DE);
Hans-Willi Krell, Penzberg (DE);
Reiner Lammers, Tuebingen (DE);
Alexander Lifke, Penzberg (DE);
Gerhard Niederfellner, Oberhausen (DE)

(73) Assignee: Hoffmann-La Roche, Inc., Little Falls, NJ (US)

( * ) Notice: Subject to any disclaimer, the term of this patent is extended or adjusted under 35 U.S.C. 154(b) by 469 days.

(21) Appl. No.: 12/868,849

(22) Filed: Aug. 26, 2010

(65) Prior Publication Data

US 2011/0070246 A1 Mar. 24, 2011

(30) Foreign Application Priority Data

Aug. 28, 2009 (EP) .................................... 09011047

(51) Int. Cl.
*A61K 39/395* (2006.01)
*A61P 35/04* (2006.01)
*C07K 16/30* (2006.01)
*C07K 16/28* (2006.01)
*C12N 15/13* (2006.01)
*C12N 15/85* (2006.01)
*C12N 5/10* (2006.01)
*A61K 39/00* (2006.01)

(52) U.S. Cl.
CPC ....... *C07K 16/2896* (2013.01); *A61K 2039/505* (2013.01); *C07K 2316/96* (2013.01); *C07K 2317/24* (2013.01); *C07K 2317/565* (2013.01); *C07K 2317/73* (2013.01)
USPC .................... 424/174.1; 530/387.1; 530/387.3

(58) Field of Classification Search
CPC .................... A61K 2039/505; C07K 2316/96; C07K 2317/24; C07K 2317/565; C07K 16/2896; C07K 2317/73
USPC .......................... 424/174.1; 530/387.1, 387.3
See application file for complete search history.

(56) References Cited

U.S. PATENT DOCUMENTS

| 7,541,030 B2 * | 6/2009 | Buehring et al. .......... 424/141.1 |
| 7,741,114 B2 * | 6/2010 | Buehring et al. ............. 435/325 |
| 2004/0053343 A1 | 3/2004 | Buehring et al. |
| 2010/0179306 A1 * | 7/2010 | Buehring et al. .......... 530/387.9 |
| 2011/0052582 A1 * | 3/2011 | Auer et al. ................. 424/133.1 |

FOREIGN PATENT DOCUMENTS

| EP | 1396501 | 3/2004 |
| JP | 2007-112734 | 5/2007 |
| WO | 02/04508 | 1/2002 |
| WO | 02/04504 | 2/2002 |
| WO | 2004/074481 | 9/2004 |
| WO | 2005/042102 | 5/2005 |
| WO | 2007/005502 | 1/2007 |
| WO | 2008/133851 | 11/2008 |

OTHER PUBLICATIONS

Buhring, Hans-Jorg et al., "CDCP1 Identifies a Broad Spectrum of Normal and Malignant Stem/Progenitor Cell Subsets of Hematopoietic and Nonhematopoietic Origin" *Stem Cells* (XP-002495598)22:334-343 (2004).
Conze, Tim et al., "CDCP1 Is a Novel Marker for Hematopoietic Stem Cells" *N.Y. Acad. Sci.* (XP-009021998)996:222-226 (2003).
European Search Report dated Dec. 18, 2009, received in priority EP Application No. EP 09011047.9.
Nezu, Jun-Ichi et al., "Identification of CDCP1 as a novel molecular target of anti-cancer therapeutic antibody targeting prostate cancer" *Abstract* (Proceedings of the Annual Meeting of the American Assoication for Cancer Research; 98th Annual Meeting of the American Association for Cancer Research), Apr. 14-18, 2007.
Scherl-Mostageer, M. et al., "Identification of a novel gene, CDCP1, overexpressed in human colorectal cancer" *Oncogene*20:4402-4408 (2001).
Siva, Amara C. et al., "Targeting CUB Domain-Containing Protein 1 with a Monoclonal Antibody Inhibits Metastatsis in a Prostate Cancer Model" *Cancer Research* (XP-002559247) 68(10):3759-3766 (May 15, 2008).
Partial International Search Report dated Oct. 6, 2010, received in International Application No. PCT/EP2010/005245.

* cited by examiner

*Primary Examiner* — Lynn Bristol
(74) *Attorney, Agent, or Firm* — Janet M. Martineau

(57) ABSTRACT

The present invention relates to antibodies against human CDCP1 binding to the same epitope as CUB4 (Deposition No. DSM ACC2551) for the treatment of cancer.

10 Claims, 10 Drawing Sheets

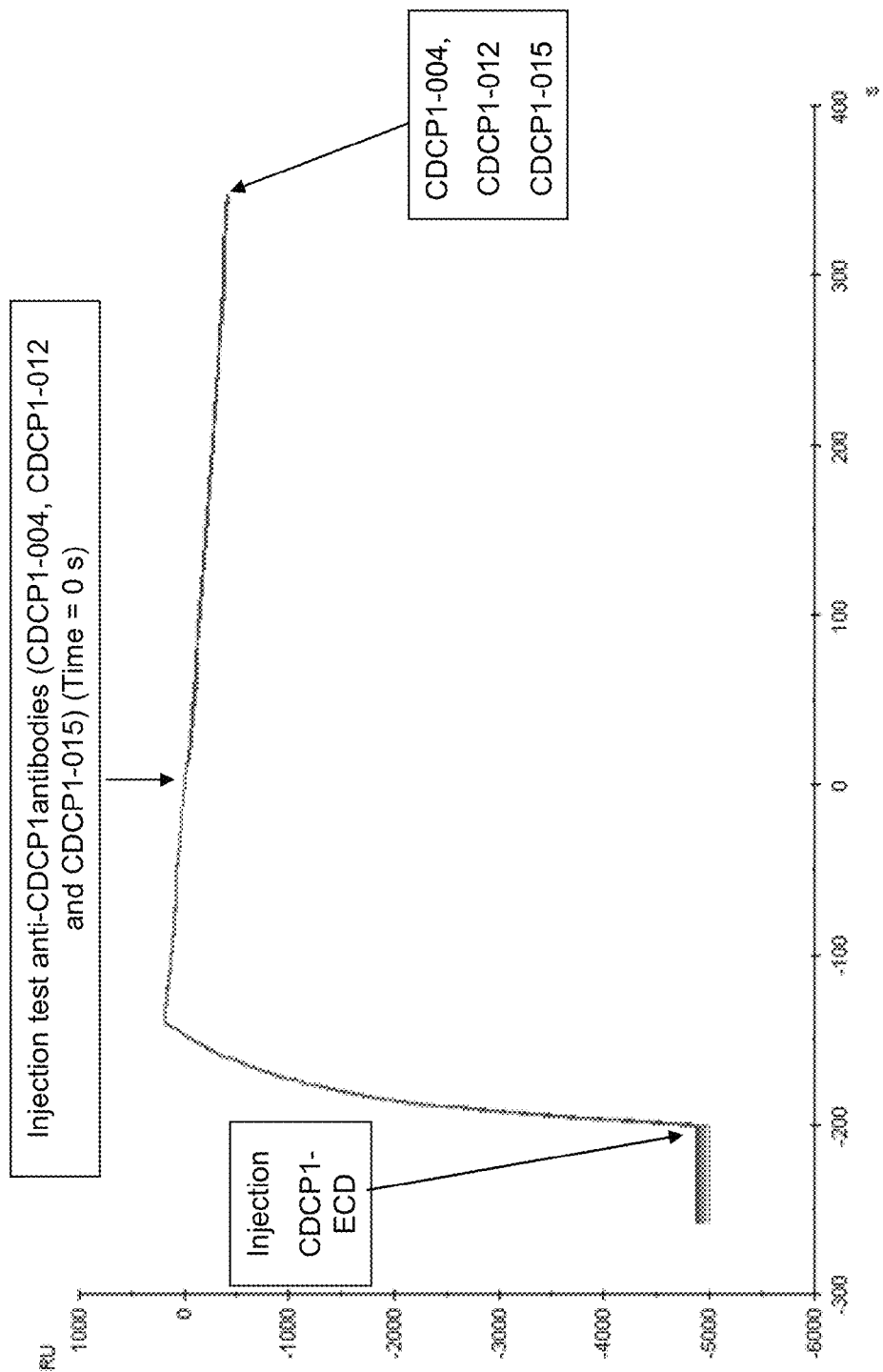

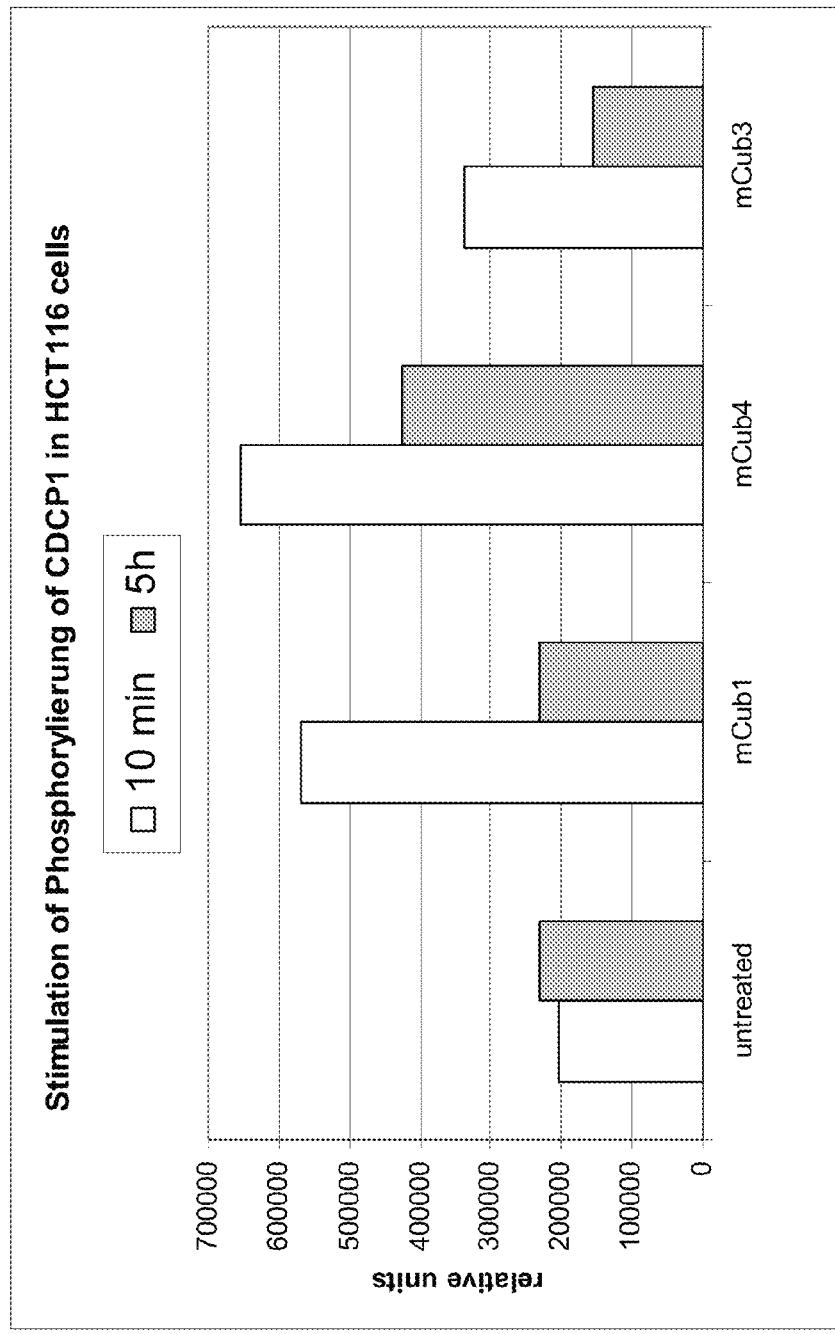

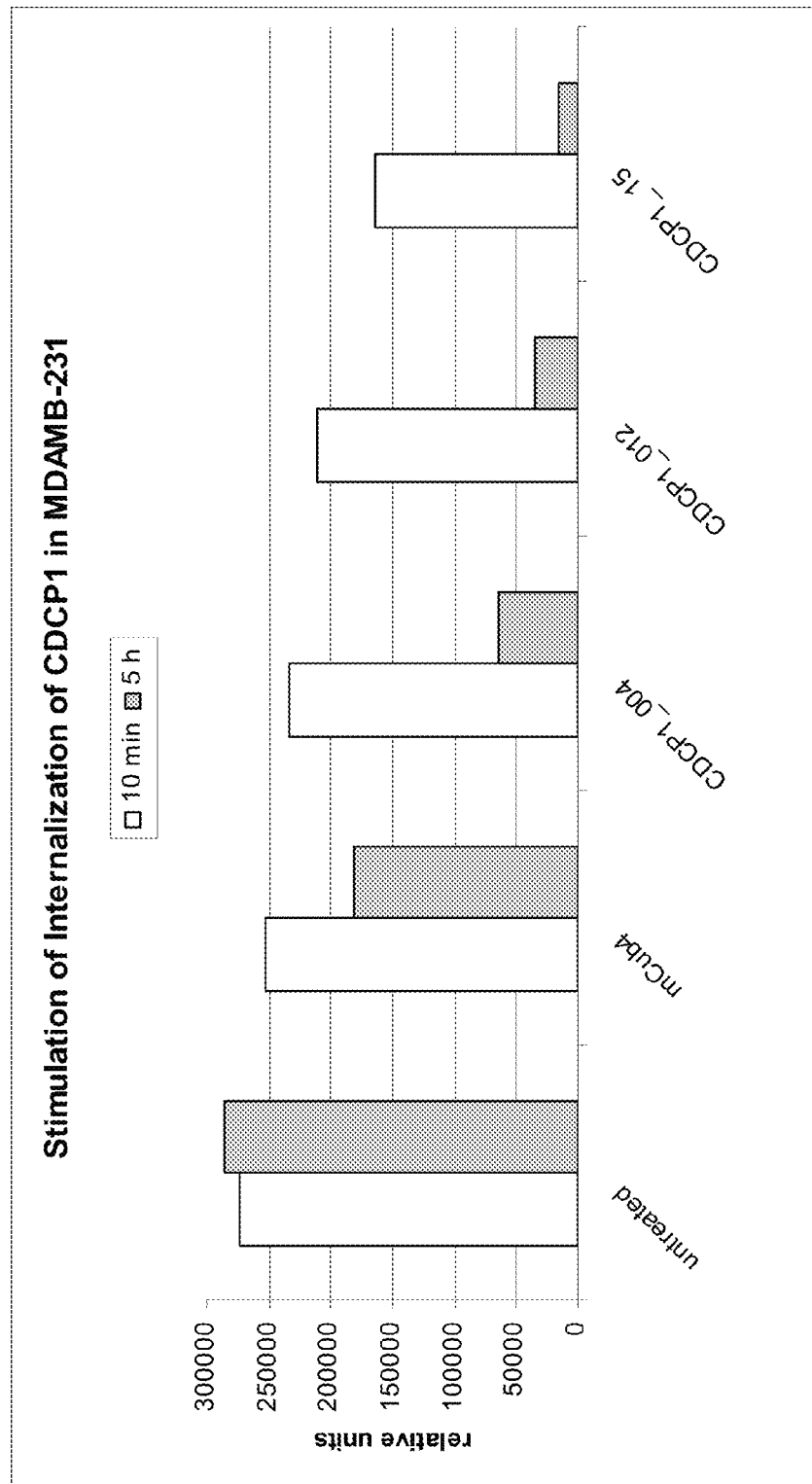

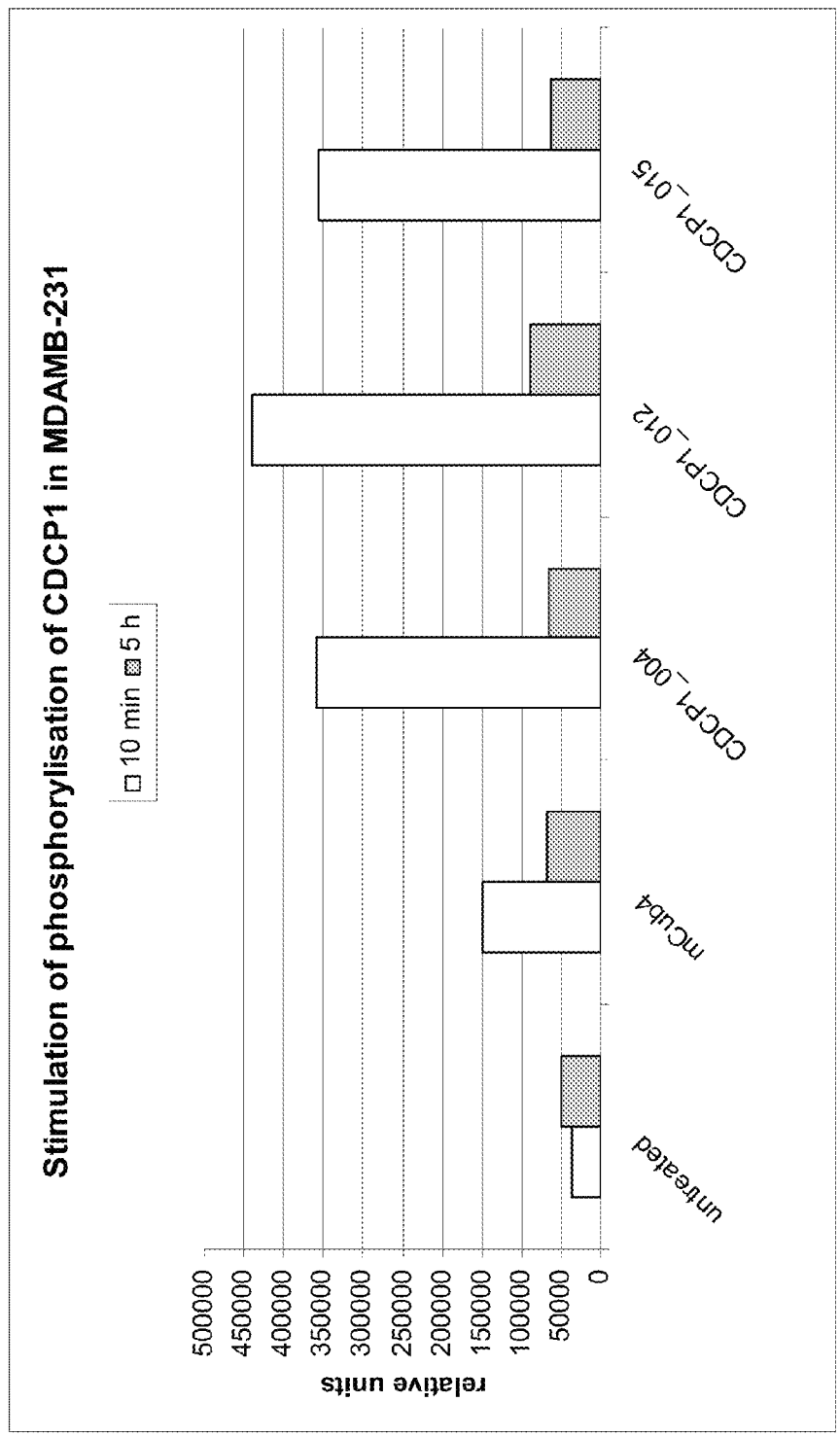

SEQUENCE LISTING

<160> NUMBER OF SEQ ID NOS: 32

<210> SEQ ID NO 1
<211> LENGTH: 836
<212> TYPE: PRT
<213> ORGANISM: Homo sapiens

<400> SEQUENCE: 1

```
Met Ala Gly Leu Asn Cys Gly Val Ser Ile Ala Leu Leu Gly Val Leu
1               5                   10                  15

Leu Leu Gly Ala Ala Arg Leu Pro Arg Gly Ala Glu Ala Phe Glu Ile
            20                  25                  30

Ala Leu Pro Arg Glu Ser Asn Ile Thr Val Leu Ile Lys Leu Gly Thr
        35                  40                  45

Pro Thr Leu Leu Ala Lys Pro Cys Tyr Ile Val Ile Ser Lys Arg His
    50                  55                  60

Ile Thr Met Leu Ser Ile Lys Ser Gly Glu Arg Ile Val Phe Thr Phe
65                  70                  75                  80

Ser Cys Gln Ser Pro Glu Asn His Phe Val Ile Glu Ile Gln Lys Asn
                85                  90                  95

Ile Asp Cys Met Ser Gly Pro Cys Pro Phe Gly Glu Val Gln Leu Gln
            100                 105                 110

Pro Ser Thr Ser Leu Leu Pro Thr Leu Asn Arg Thr Phe Ile Trp Asp
        115                 120                 125

Val Lys Ala His Lys Ser Ile Gly Leu Glu Leu Gln Phe Ser Ile Pro
    130                 135                 140

Arg Leu Arg Gln Ile Gly Pro Gly Glu Ser Cys Pro Asp Gly Val Thr
145                 150                 155                 160

His Ser Ile Ser Gly Arg Ile Asp Ala Thr Val Val Arg Ile Gly Thr
                165                 170                 175

Phe Cys Ser Asn Gly Thr Val Ser Arg Ile Lys Met Gln Glu Gly Val
            180                 185                 190

Lys Met Ala Leu His Leu Pro Trp Phe His Pro Arg Asn Val Ser Gly
        195                 200                 205

Phe Ser Ile Ala Asn Arg Ser Ser Ile Lys Arg Leu Cys Ile Ile Glu
    210                 215                 220

Ser Val Phe Glu Gly Glu Gly Ser Ala Thr Leu Met Ser Ala Asn Tyr
```

```
            225                 230                 235                 240

Pro Glu Gly Phe Pro Glu Asp Glu Leu Met Thr Trp Gln Phe Val Val
                        245                 250                 255

Pro Ala His Leu Arg Ala Ser Val Ser Phe Leu Asn Phe Asn Leu Ser
                        260                 265                 270

Asn Cys Glu Arg Lys Glu Arg Val Glu Tyr Tyr Ile Pro Gly Ser
                        275                 280                 285

Thr Thr Asn Pro Glu Val Phe Lys Leu Glu Asp Lys Gln Pro Gly Asn
                        290                 295                 300

Met Ala Gly Asn Phe Asn Leu Ser Leu Gln Gly Cys Asp Gln Asp Ala
        305                 310                 315                 320

Gln Ser Pro Gly Ile Leu Arg Leu Gln Phe Gln Val Leu Val Gln His
                        325                 330                 335

Pro Gln Asn Glu Ser Asn Lys Ile Tyr Val Val Asp Leu Ser Asn Glu
                        340                 345                 350

Arg Ala Met Ser Leu Thr Ile Glu Pro Arg Pro Val Lys Gln Ser Arg
                        355                 360                 365

Lys Phe Val Pro Gly Cys Phe Val Cys Leu Glu Ser Arg Thr Cys Ser
                        370                 375                 380

Ser Asn Leu Thr Leu Thr Ser Gly Ser Lys His Lys Ile Ser Phe Leu
        385                 390                 395                 400

Cys Asp Asp Leu Thr Arg Leu Trp Met Asn Val Glu Lys Thr Ile Ser
                        405                 410                 415

Cys Thr Asp His Arg Tyr Cys Gln Arg Lys Ser Tyr Ser Leu Gln Val
                        420                 425                 430

Pro Ser Asp Ile Leu His Leu Pro Val Glu Leu His Asp Phe Ser Trp
                        435                 440                 445

Lys Leu Leu Val Pro Lys Asp Arg Leu Ser Leu Val Leu Val Pro Ala
                        450                 455                 460

Gln Lys Leu Gln Gln His Thr His Glu Lys Pro Cys Asn Thr Ser Phe
        465                 470                 475                 480

Ser Tyr Leu Val Ala Ser Ala Ile Pro Ser Gln Asp Leu Tyr Phe Gly
                        485                 490                 495

Ser Phe Cys Pro Gly Gly Ser Ile Lys Gln Ile Gln Val Lys Gln Asn
                        500                 505                 510

Ile Ser Val Thr Leu Arg Thr Phe Ala Pro Ser Phe Arg Gln Glu Ala
                        515                 520                 525

Ser Arg Gln Gly Leu Thr Val Ser Phe Ile Pro Tyr Phe Lys Glu Glu
                        530                 535                 540

Gly Val Phe Thr Val Thr Pro Asp Thr Lys Ser Lys Val Tyr Leu Arg
        545                 550                 555                 560

Thr Pro Asn Trp Asp Arg Gly Leu Pro Ser Leu Thr Ser Val Ser Trp
                        565                 570                 575

Asn Ile Ser Val Pro Arg Asp Gln Val Ala Cys Leu Thr Phe Phe Lys
                        580                 585                 590

Glu Arg Ser Gly Val Val Cys Gln Thr Gly Arg Ala Phe Met Ile Ile
                        595                 600                 605

Gln Glu Gln Arg Thr Arg Ala Glu Glu Ile Phe Ser Leu Asp Glu Asp
                        610                 615                 620

Val Leu Pro Lys Pro Ser Phe His His Ser Phe Trp Val Asn Ile
        625                 630                 635                 640

Ser Asn Cys Ser Pro Thr Ser Gly Lys Gln Leu Asp Leu Leu Phe Ser
                        645                 650                 655
```

```
Val Thr Leu Thr Pro Arg Thr Val Asp Leu Thr Val Ile Leu Ile Ala
            660                 665                 670

Ala Val Gly Gly Gly Val Leu Leu Ser Ala Leu Gly Leu Ile Ile
        675                 680                 685

Cys Cys Val Lys Lys Lys Lys Thr Asn Lys Gly Pro Ala Val
690                 695                 700

Gly Ile Tyr Asn Gly Asn Ile Asn Thr Glu Met Pro Arg Gln Pro Lys
705                 710                 715                 720

Lys Phe Gln Lys Gly Arg Lys Asp Asn Asp Ser His Val Tyr Ala Val
                725                 730                 735

Ile Glu Asp Thr Met Val Tyr Gly His Leu Leu Gln Asp Ser Ser Gly
            740                 745                 750

Ser Phe Leu Gln Pro Glu Val Asp Thr Tyr Arg Pro Phe Gln Gly Thr
        755                 760                 765

Met Gly Val Cys Pro Pro Ser Pro Pro Thr Ile Cys Ser Arg Ala Pro
    770                 775                 780

Thr Ala Lys Leu Ala Thr Glu Glu Pro Pro Pro Arg Ser Pro Pro Glu
785                 790                 795                 800

Ser Glu Ser Glu Pro Tyr Thr Phe Ser His Pro Asn Asn Gly Asp Val
                805                 810                 815

Ser Ser Lys Asp Thr Asp Ile Pro Leu Leu Asn Thr Gln Glu Pro Met
            820                 825                 830

Glu Pro Ala Glu
        835

<210> SEQ ID NO 2
<211> LENGTH: 663
<212> TYPE: PRT
<213> ORGANISM: Homo sapiens

<400> SEQUENCE: 2

Met Ala Gly Leu Asn Cys Gly Val Ser Ile Ala Leu Leu Gly Val Leu
1               5                   10                  15

Leu Leu Gly Ala Ala Arg Leu Pro Arg Gly Ala Glu Ala Phe Glu Ile
            20                  25                  30

Ala Leu Pro Arg Glu Ser Asn Ile Thr Val Leu Ile Lys Leu Gly Thr
        35                  40                  45

Pro Thr Leu Leu Ala Lys Pro Cys Tyr Ile Val Ile Ser Lys Arg His
    50                  55                  60

Ile Thr Met Leu Ser Ile Lys Ser Gly Glu Arg Ile Val Phe Thr Phe
65                  70                  75                  80

Ser Cys Gln Ser Pro Glu Asn His Phe Val Ile Glu Ile Gln Lys Asn
                85                  90                  95

Ile Asp Cys Met Ser Gly Pro Cys Pro Phe Gly Glu Val Gln Leu Gln
            100                 105                 110

Pro Ser Thr Ser Leu Leu Pro Thr Leu Asn Arg Thr Phe Ile Trp Asp
        115                 120                 125

Val Lys Ala His Lys Ser Ile Gly Leu Glu Leu Gln Phe Ser Ile Pro
    130                 135                 140

Arg Leu Arg Gln Ile Gly Pro Gly Glu Ser Cys Pro Asp Gly Val Thr
145                 150                 155                 160

His Ser Ile Ser Gly Arg Ile Asp Ala Thr Val Val Arg Ile Gly Thr
                165                 170                 175

Phe Cys Ser Asn Gly Thr Val Ser Arg Ile Lys Met Gln Glu Gly Val
```

-continued

```
                180                 185                 190
Lys Met Ala Leu His Leu Pro Trp Phe His Pro Arg Asn Val Ser Gly
            195                 200                 205

Phe Ser Ile Ala Asn Arg Ser Ser Ile Lys Arg Leu Cys Ile Ile Glu
        210                 215                 220

Ser Val Phe Glu Gly Glu Gly Ser Ala Thr Leu Met Ser Ala Asn Tyr
225                 230                 235                 240

Pro Glu Gly Phe Pro Glu Asp Glu Leu Met Thr Trp Gln Phe Val Val
                245                 250                 255

Pro Ala His Leu Arg Ala Ser Val Ser Phe Leu Asn Phe Asn Leu Ser
            260                 265                 270

Asn Cys Glu Arg Lys Glu Arg Val Glu Tyr Tyr Ile Pro Gly Ser
        275                 280                 285

Thr Thr Asn Pro Glu Val Phe Lys Leu Glu Asp Lys Gln Pro Gly Asn
        290                 295                 300

Met Ala Gly Asn Phe Asn Leu Ser Leu Gln Gly Cys Asp Gln Asp Ala
305                 310                 315                 320

Gln Ser Pro Gly Ile Leu Arg Leu Gln Phe Gln Val Leu Val Gln His
                325                 330                 335

Pro Gln Asn Glu Ser Asn Lys Ile Tyr Val Val Asp Leu Ser Asn Glu
            340                 345                 350

Arg Ala Met Ser Leu Thr Ile Glu Pro Arg Pro Val Lys Gln Ser Arg
        355                 360                 365

Lys Phe Val Pro Gly Cys Phe Val Cys Leu Glu Ser Arg Thr Cys Ser
        370                 375                 380

Ser Asn Leu Thr Leu Thr Ser Gly Ser Lys His Lys Ile Ser Phe Leu
385                 390                 395                 400

Cys Asp Asp Leu Thr Arg Leu Trp Met Asn Val Glu Lys Thr Ile Ser
                405                 410                 415

Cys Thr Asp His Arg Tyr Cys Gln Arg Lys Ser Tyr Ser Leu Gln Val
            420                 425                 430

Pro Ser Asp Ile Leu His Leu Pro Val Glu Leu His Asp Phe Ser Trp
        435                 440                 445

Lys Leu Leu Val Pro Lys Asp Arg Leu Ser Leu Val Leu Val Pro Ala
        450                 455                 460

Gln Lys Leu Gln Gln His Thr His Glu Lys Pro Cys Asn Thr Ser Phe
465                 470                 475                 480

Ser Tyr Leu Val Ala Ser Ala Ile Pro Ser Gln Asp Leu Tyr Phe Gly
                485                 490                 495

Ser Phe Cys Pro Gly Gly Ser Ile Lys Gln Ile Gln Val Lys Gln Asn
            500                 505                 510

Ile Ser Val Thr Leu Arg Thr Phe Ala Pro Ser Phe Arg Gln Glu Ala
        515                 520                 525

Ser Arg Gln Gly Leu Thr Val Ser Phe Ile Pro Tyr Phe Lys Glu Glu
        530                 535                 540

Gly Val Phe Thr Val Thr Pro Asp Thr Lys Ser Lys Val Tyr Leu Arg
545                 550                 555                 560

Thr Pro Asn Trp Asp Arg Gly Leu Pro Ser Leu Thr Ser Val Ser Trp
                565                 570                 575

Asn Ile Ser Val Pro Arg Asp Gln Val Ala Cys Leu Thr Phe Phe Lys
            580                 585                 590

Glu Arg Ser Gly Val Val Cys Gln Thr Gly Arg Ala Phe Met Ile Ile
        595                 600                 605
```

Gln Glu Gln Arg Thr Arg Ala Glu Glu Ile Phe Ser Leu Asp Glu Asp
            610                 615                 620

Val Leu Pro Lys Pro Ser Phe His His His Ser Phe Trp Val Asn Ile
625                 630                 635                 640

Ser Asn Cys Ser Pro Thr Ser Gly Lys Gln Leu Asp Leu Leu Phe Ser
            645                 650                 655

Val Thr Leu Thr Pro Arg Thr
            660

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr

```
            305                 310                 315                 320
Gln Lys Ser Leu Ser Leu Ser Pro Gly Lys
                325                 330

<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 104
<212> TYPE: PRT
<213> ORGANISM: Homo sapiens

<400> SEQUENCE: 5

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 6
<211> LENGTH: 327
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 7
<211> LENGTH: 120
<212> TYPE: PRT
<213> ORGANISM: Mus musculus

<400> SEQUENCE: 7

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Asn Ser Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
            50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys

```
                    85                  90                  95

Ala Arg His Pro Asp Tyr Asp Gly Val Trp Phe Ala Tyr Trp Gly Gln
                100                 105                 110

Gly Thr Leu Val Thr Val Ser Ala
            115                 120

<210> SEQ ID NO 8
<211> LENGTH: 106
<212> TYPE: PRT
<213> ORGANISM: Mus musculus

<400> SEQUENCE: 8

Gln Ile Val Leu Thr Gln Ser Pro Ala Ile Met Ser Ala Ser Pro Gly
1               5                   10                  15

Glu Lys Val Thr Met Thr Cys Ser Val Ser Ser Ser Val Phe Tyr Val
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Pro Thr
                85                  90                  95

Phe Gly Gly Gly Thr Lys Leu Glu Ile Lys
                100                 105

<210> SEQ ID NO 9
<211> LENGTH: 7
<212> TYPE: PRT
<213> ORGANISM: Mus musculus

<400> SEQUENCE: 9

Thr Ala Gly Val Gly Val Ser
1               5

<210> SEQ ID NO 10
<211> LENGTH: 16
<212> TYPE: PRT
<213> ORGANISM: Mus musculus

<400> SEQUENCE: 10

His Ile Tyr Trp Asp Asp Asp Lys Arg Tyr Asn Pro Ser Leu Lys Ser
1               5                   10                  15

<210> SEQ ID NO 11
<211> LENGTH: 10
<212> TYPE: PRT
<213> ORGANISM: Mus musculus

<400> SEQUENCE: 11

Ser Thr Ser Val Glu Glu Ala Phe Asp Val
1               5                   10

<210> SEQ ID NO 12
<211> LENGTH: 16
<212> TYPE: PRT
<213> ORGANISM: Mus musculus

<400> SEQUENCE: 12

Arg Ser Ser Gln Asn Ile Val His Ser Tyr Gly Asn Thr Tyr Leu Glu
```

```
1               5                   10                  15
```

<210> SEQ ID NO 13
<211> LENGTH: 7
<212> TYPE: PRT
<213> ORGANISM: Mus musculus

<400> SEQUENCE: 13

Lys Val Ser Asn Arg Phe Ser
1               5

<210> SEQ ID NO 14
<211> LENGTH: 9
<212> TYPE: PRT
<213> ORGANISM: Mus musculus

<400> SEQUENCE: 14

Phe Gln Gly Ser His Val Pro Trp Thr
1               5

<210> SEQ ID NO 15
<211> LENGTH: 120
<212> TYPE: PRT
<213> ORGANISM: Mus musculus

<400> SEQUENCE: 15

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ala
            20                  25                  30

Gly Val Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Lys Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Ser Ala Asp Thr Ala Thr Tyr Phe
                85                  90                  95

Cys Ser Arg Ser Thr Ser Val Glu Glu Ala Phe Asp Val Trp Gly Ala
            100                 105                 110

Gly Thr Thr Val Thr Val Ser Ser
        115                 120

<210> SEQ ID NO 16
<211> LENGTH: 112
<212> TYPE: PRT
<213> ORGANISM: Mus musculus

<400> SEQUENCE: 16

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Tyr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Trp Thr Phe Gly Gly Gly Thr Lys Leu Glu Ile Lys
            100                 105                 110

<210> SEQ ID NO 17
<211> LENGTH: 7
<212> TYPE: PRT
<213> ORGANISM: Mus musculus

<400> SEQUENCE: 17

Thr Ala Gly Met Gly Val Ser
1               5

<210> SEQ ID NO 18
<211> LENGTH: 16
<212> TYPE: PRT
<213> ORGANISM: Mus musculus

<400> SEQUENCE: 18

His Ile Tyr Trp Asp Asp Asp Lys Arg Tyr Asn Pro Ser Leu Lys Ser
1               5                   10                  15

<210> SEQ ID NO 19
<211> LENGTH: 9
<212> TYPE: PRT
<213> ORGANISM: Mus musculus

<400> SEQUENCE: 19

Ser Asp Ser Phe Gly Asp Phe Asp Tyr
1               5

<210> SEQ ID NO 20
<211> LENGTH: 16
<212> TYPE: PRT
<213> ORGANISM: Mus musculus

<400> SEQUENCE: 20

Lys Ser Ser Gln Ser Leu Leu Tyr Thr Asn Gly Lys Thr Tyr Leu Ile
1               5                   10                  15

<210> SEQ ID NO 21
<211> LENGTH: 7
<212> TYPE: PRT
<213> ORGANISM: Mus musculus

<400> SEQUENCE: 21

Leu Val Ser Lys Leu Asp Ser
1               5

<210> SEQ ID NO 22
<211> LENGTH: 9
<212> TYPE: PRT
<213> ORGANISM: Mus musculus

<400> SEQUENCE: 22

Leu Gln Ser Thr His Phe Pro Tyr Thr
1               5

<210> SEQ ID NO 23
<211> LENGTH: 119
<212> TYPE: PRT
<213> ORGANISM: Mus musculus

<400> SEQUENCE: 23

```
Gln Val Thr Leu Lys Glu Ser Gly Pro Gly Ile Leu Gln Ser Ser Gln
1               5                  10                 15

Thr Leu Ser Leu Thr Cys Ser Phe Ser Gly Phe Ser Leu Ser Thr Ala
            20                 25                 30

Gly Met Gly Val Ser Trp Ile Arg Gln Pro Ser Gly Lys Gly Leu Glu
        35                 40                 45

Trp Leu Ala His Ile Tyr Trp Asp Asp Asp Lys Arg Tyr Asn Pro Ser
50                  55                 60

Leu Lys Ser Arg Leu Thr Val Ser Lys Gly Thr Ser Arg Asn Gln Val
65                  70                 75                 80

Leu Leu Lys Ile Thr Ser Val Asp Ala Ala Asp Thr Ala Thr Tyr Tyr
                85                 90                 95

Cys Ala Arg Ser Asp Ser Phe Gly Asp Phe Asp Tyr Trp Gly Gln Gly
            100                105                110

Thr Thr Leu Thr Val Ser Ser
            115

<210> SEQ ID NO 24
<211> LENGTH: 112
<212> TYPE: PRT
<213> ORGANISM: Mus musculus

<400> SEQUENCE: 24

Asp Val Val Met Thr Gln Thr Pro Leu Thr Leu Ser Val Thr Ile Gly
1               5                  10                 15

Gln Pro Ala Ser Ile Ser Cys Lys Ser Ser Gln Ser Leu Leu Tyr Thr
            20                 25                 30

Asn Gly Lys Thr Tyr Leu Ile Trp Leu Leu Gln Arg Pro Gly Gln Ser
        35                 40                 45

Pro Lys Arg Leu Ile Tyr Leu Val Ser Lys Leu Asp Ser Gly Val Pro
50                  55                 60

Asp Arg Phe Ser Gly Ser Gly Ser Gly Thr Asp Phe Thr Leu Lys Ile
65                  70                 75                 80

Ser Arg Val Glu Ala Glu Asp Leu Gly Val Tyr Tyr Cys Leu Gln Ser
                85                 90                 95

Thr His Phe Pro Tyr Thr Phe Gly Gly Gly Thr Lys Leu Glu Ile Lys
            100                105                110

<210> SEQ ID NO 25
<211> LENGTH: 5
<212> TYPE: PRT
<213> ORGANISM: Mus musculus

<400> SEQUENCE: 25

Asn Phe Gly Leu His
1               5

<210> SEQ ID NO 26
<211> LENGTH: 16
<212> TYPE: PRT
<213> ORGANISM: Mus musculus

<400> SEQUENCE: 26

Val Ile Trp Ser Gly Gly Val Thr Asp Tyr Asn Ala Ala Phe Ile Ser
1               5                  10                 15

<210> SEQ ID NO 27
<211> LENGTH: 10
```

```
<212> TYPE: PRT
<213> ORGANISM: Mus musculus

<400> SEQUENCE: 27

Asn Tyr Asp His Asp Tyr Ser Met Asp Tyr
1               5                   10

<210> SEQ ID NO 28
<211> LENGTH: 16
<212> TYPE: PRT
<213> ORGANISM: Mus musculus

<400> SEQUENCE: 28

Lys Ser Thr Lys Ser Leu Leu Asn Ser Ala Gly Phe Thr Tyr Leu Gly
1               5                   10                  15

<210> SEQ ID NO 29
<211> LENGTH: 7
<212> TYPE: PRT
<213> ORGANISM: Mus musculus

<400> SEQUENCE: 29

Leu Val Ser Asn Arg Phe Ser
1               5

<210> SEQ ID NO 30
<211> LENGTH: 9
<212> TYPE: PRT
<213> ORGANISM: Mus musculus

<400> SEQUENCE: 30

Phe Gln Ser Ser Tyr Leu Pro Leu Thr
1               5

<210> SEQ ID NO 31
<211> LENGTH: 118
<212> TYPE: PRT
<213> ORGANISM: Mus musculus

<400> SEQUENCE: 31

Gln Val His Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Phe
                20                  25                  30

Gly Leu His Trp Val Arg Gln Ser Pro Gly Lys Gly Leu Glu Trp Leu
            35                  40                  45

Gly Val Ile Trp Ser Gly Gly Val Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Pro Asn Asp Thr Ala Ile Tyr Tyr Cys Ala
                85                  90                  95

Arg Asn Tyr Asp His Asp Tyr Ser Met Asp Tyr Trp Gly Gln Gly Ile
                100                 105                 110

Ser Val Ser Val Ser Ser
            115

<210> SEQ ID NO 32
<211> LENGTH: 112
<212> TYPE: PRT
<213> ORGANISM: Mus musculus
```

```
<400> SEQUENCE: 32

Asp Val Val Leu Thr Gln Thr Pro Leu Ser Leu Pro Val Ile Ile Gly
1               5                   10                  15

Asp Gln Ala Ser Ile Ser Cys Lys Ser Thr Lys Ser Leu Leu Asn Ser
            20                  25                  30

Ala Gly Phe Thr Tyr Leu Gly Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Ser
                85                  90                  95

Ser Tyr Leu Pro Leu Thr Phe Gly Ser Gly Thr Lys Leu Glu Ile Lys
            100                 105                 110
```

ANTIBODIES AGAINST CDCP1 FOR THE TREATMENT OF CANCER

CROSS-REFERENCE TO RELATED APPLICATIONS

This application claims the benefit of the filing date of European patent application 09011047.9, filed Aug. 28, 2009, the contents of which are hereby incorporated by reference.

FIELD OF INVENTION

The present invention relates to antibodies against human CDCP1 binding to the same epitope as CUB4 (Deposition No. DSM ACC2551) for the treatment of cancer.

BACKGROUND OF THE INVENTION

Human CDCP1 ((CUB domain containing protein 1, B345, CD318, SIMA135, TRASK; SEQ ID NO: 1 and variants with mutation R525Q (i.e. replacement of Arginine (R) with Glutamine (Q) at amino acid position 525 of SEQ ID NO: 1) and/or mutation G709D (i.e. replacement of Glycine (G) with Aspartic acid (D) at amino acid position 709 of SEQ ID NO: 1)) is a transmembrane protein containing three extracellular CUB domains. This protein is found to be overexpressed in colon and lung cancers. Its expression level is correlated with the metastatic ability of carcinoma cells. It has been shown to be tyrosine phosphorylated in a cancer cell line. (WO 2002/004508; Scherl-Mostageer, M. et al., Oncogene 20 (2001) 4402-8; Hooper, J. D., et al., Oncogene 22 (2003) 1783-94; Perry, S. E. et al., FEBS Lett. 581 (2007) 1137-42; Brown, T. A., J. Biol. Chem. 279 (2004) 14772-14783; Ota, T., et al., Nat. Genet. 36 (2004) 40-45). Alternatively spliced transcript variants encoding distinct isoforms have been reported.

WO 2002/004508 refers to CDCP1 as tumor associated antigen B345. WO 2004/074481 relates to CDCP1 as glycoprotein antigen SIMA135 expressed in metastatic tumor cells. WO 2005/042102 relates to CDCP1 as protein involved in ovarian cancer. WO 2007/005502 relates to methods and compositions for treating diseases targeting CDCP1.

US 2004/0053343 (and Conze, T. et al., Ann. N.Y. Acad. Sci. 996 (2003) 222-6 and Buhring, H. J. et al., Stem Cells 22 (2004) 334-43) relates to CDCP1 antibodies for identifying and/or certain cell stem cell populations.

SUMMARY OF THE INVENTION

One aspect of the invention is an antibody specifically binding to human CDCP1 characterized in binding to same epitope as CUB4 (Deposition No. DSM ACC2551) for the treatment of cancer.

The invention further comprises an antibody characterized in binding to same epitope as CUB4 (Deposition No. DSM ACC2551) for the treatment of cancer, and further characterized in that
   a) the heavy chain variable domain is SEQ ID NO: 7 and the light chain variable domain is SEQ ID NO: 8,
   b) the heavy chain variable domain is SEQ ID NO: 15 and the light chain variable domain is SEQ ID NO: 16, or
   c) the heavy chain variable domain is SEQ ID NO: 23 and the light chain variable domain is SEQ ID NO: 24, or
   d) the heavy chain variable domain is SEQ ID NO: 31 and the light chain variable domain is SEQ ID NO: 32, or
   or a humanized version thereof.

The invention further comprises an antibody characterized in binding to same epitope as CUB4 (Deposition No. DSM ACC2551) for the treatment of cancer, and further characterized in that
   a) the heavy chain variable domain comprises a CDRH1 region of SEQ ID NO: 9, a CDRH2 region of SEQ ID NO: 10, and a CDRH3 region of SEQ ID NO: 11, and the light chain variable domain comprises a CDRL1 region of SEQ ID NO: 12, a CDRL2 region of SEQ ID NO: 13, and a CDRL3 region of SEQ ID NO: 14, or
   b) the heavy chain variable domain comprises a CDRH1 region of SEQ ID NO: 17, a CDRH2 region of SEQ ID NO: 18, and a CDRH3 region of SEQ ID NO: 19, and the light chain variable domain comprises a CDRL1 region of SEQ ID NO: 20, a CDRL2 region of SEQ ID NO: 21, and a CDRL3 region of SEQ ID NO: 22, or
   c) the heavy chain variable domain comprises a CDRH1 region of SEQ ID NO: 25, a CDRH2 region of SEQ ID NO: 26, and a CDRH3 region of SEQ ID NO: 27, and the light chain variable domain comprises a CDRL1 region of SEQ ID NO: 28, a CDRL2 region of SEQ ID NO: 29, and a CDRL3 region of SEQ ID NO: 30.

The invention further comprises an antibody according to the invention, characterized in that said antibody is of human IgG1 subclass.

Another aspect of the invention is a pharmaceutical composition comprising an antibody specifically binding to human CDCP1 characterized in binding to same epitope as CUB4 (Deposition No. DSM ACC2551), for the treatment of cancer.

Another aspect of the invention is the use of an antibody specifically binding to human CDCP1 characterized in binding to same epitope as CUB4 (Deposition No. DSM ACC2551) in the preparation of a medicament for the treatment of cancer Another aspect of the invention is a method of treatment of a patient suffering from cancer by administering an antibody specifically binding to human CDCP1 characterized in binding to same epitope as CUB4 (Deposition No. DSM ACC2551) to said patient in the need of such treatment.

The invention further comprises an antibody according to the invention, characterized in that
   a) the heavy chain variable domain is SEQ ID NO: 15 and the light chain variable domain is SEQ ID NO: 16, or
   b) the heavy chain variable domain is SEQ ID NO: 23 and the light chain variable domain is SEQ ID NO: 24, or
   c) the heavy chain variable domain is SEQ ID NO: 31 and the light chain variable domain is SEQ ID NO: 32, or
   or a humanized version thereof.

The invention further comprises an antibody according to the invention, characterized in that
   a) the heavy chain variable domain comprises a CDRH1 region of SEQ ID NO: 9, a CDRH2 region of SEQ ID NO: 10, and a CDRH3 region of SEQ ID NO: 11, and the light chain variable domain comprises a CDRL1 region of SEQ ID NO: 12, a CDRL2 region of SEQ ID NO: 13, and a CDRL3 region of SEQ ID NO: 14, or
   b) the heavy chain variable domain comprises a CDRH1 region of SEQ ID NO: 17, a CDRH2 region of SEQ ID NO: 18, and a CDRH3 region of SEQ ID NO: 19, and the light chain variable domain comprises a CDRL1 region of SEQ ID NO: 20, a CDRL2 region of SEQ ID NO: 21, and a CDRL3 region of SEQ ID NO: 22, or
   c) the heavy chain variable domain comprises a CDRH1 region of SEQ ID NO: 25, a CDRH2 region of SEQ ID NO: 26, and a CDRH3 region of SEQ ID NO: 27, and the light chain variable domain comprises a CDRL1 region of SEQ ID NO: 28, a CDRL2 region of SEQ ID NO: 29, and a CDRL3 region of SEQ ID NO: 30.

Preferably said antibody is characterized in that said antibody is of human IgG1 subclass. The invention further comprises a pharmaceutical composition comprising said antibody. The invention further comprises the of said antibody according for the preparation of a medicament for the treatment of cancer. The invention further comprises a method of treatment of a patient suffering from cancer by administering said antibody to said patient in the need of such treatment.

The invention provides nucleic acid encoding the humanized antibody according to the invention. The invention further provides expression vectors containing nucleic acid according to the invention capable of expressing said nucleic acid in a prokaryotic or eukaryotic host cell, and host cells containing such vectors for the recombinant production of an antibody according to the invention.

The invention further comprises a prokaryotic or eukaryotic host cell comprising a vector according to the invention.

The invention further comprises a method for the production of a recombinant humanized antibody according to the invention, characterized by expressing a nucleic acid according to the invention in a prokaryotic or eukaryotic host cell and recovering said antibody from said cell or the cell culture supernatant. The invention further comprises the antibody obtained by such a recombinant method.

It has now surprisingly been found that the antibodies specifically binding to CDCP1 characterized in binding to same epitope as CUB4 (Deposition No. DSM ACC2551) are especially useful for the treatment of cancer compared to CDCP1 antibodies binding to other epitopes of CDCP1 like e.g. CUB1 (Deposition No. DSM ACC2569).

DESCRIPTION OF THE FIGURES

FIG. 3 Biacore sensogram of immobilized CUB4 antibody, extracellular domain (ECD) of CDCP1 and anti-CDCP1 antibodies CUB1 and CUB3 (x-axis=time; y-axis=response in relative units (RU))

FIG. 3a: The binding of CDCP1-004, CDCP1-012 and CDCP1-015 antibodies to the same epitope on CDCP1 as CUB4 antibody is shown.

DETAILED DESCRIPTION OF THE INVENTION

Figure 1:
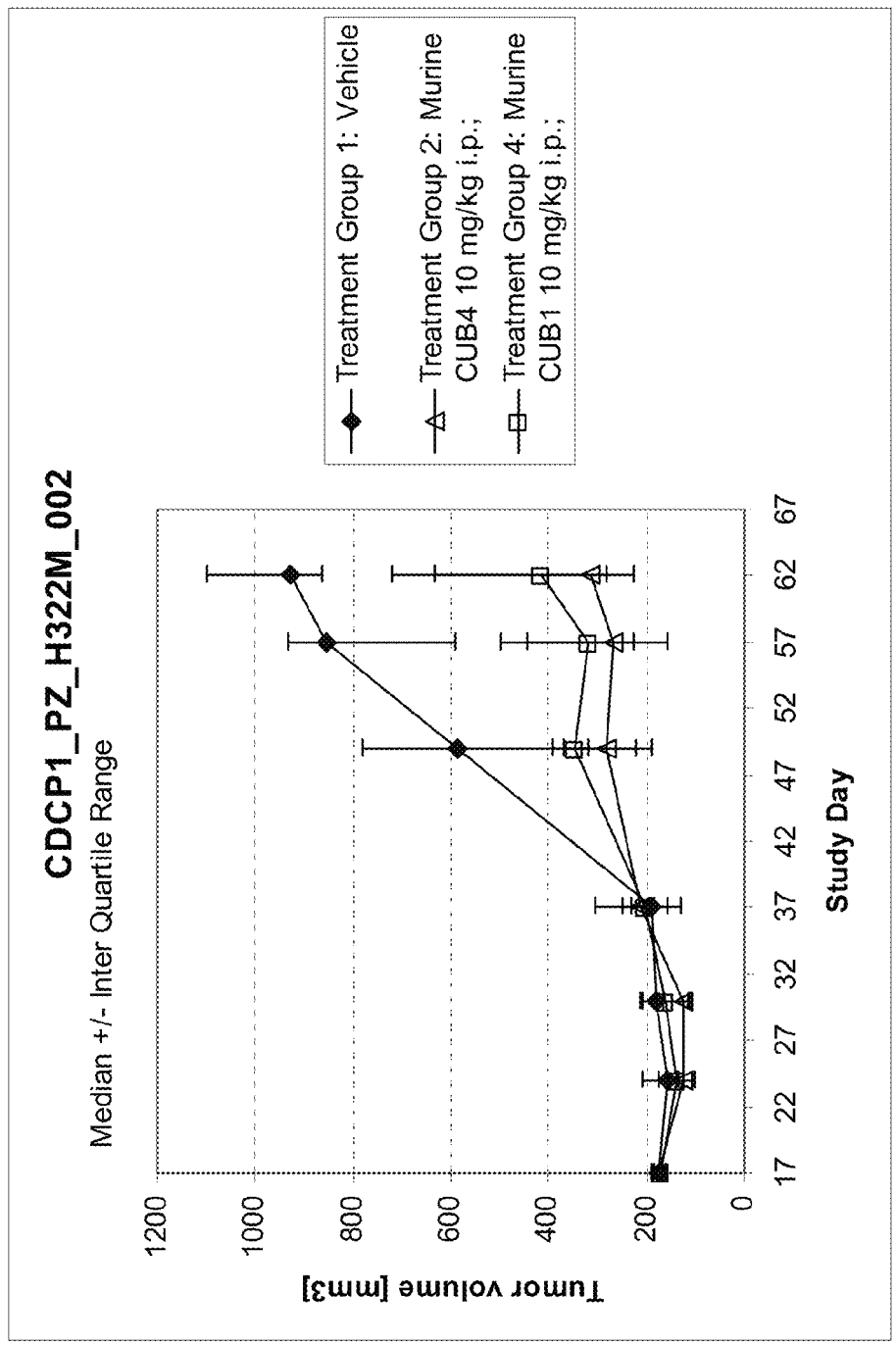
FIG. 1 In vivo tumor growth inhibition in human lung cancer H322M xenograft of anti CDCP1 antibodies CUB4 and CUB.

The CUB4 antibody refers to the deposited antibody with the Deposition No. DSM ACC2551 from DE 10242146 (EP 1 396 501, U.S. Pat. No. 7,541,030) with the heavy chain variable domain (VH) of SEQ ID NO: 7 and the light chain variable domain (VL) of SEQ ID NO: 8. Said CUB4 antibody is specifically binding to human CDCP1.

The invention comprises an antibody specifically binding to human CDCP1 characterized in binding to same epitope as CUB4 (Deposition No. DSM ACC2551) for the treatment of cancer.

The invention further comprises an antibody according to the invention, characterized in that
the heavy chain variable domain is SEQ ID NO: 7 and the light chain variable domain is SEQ ID NO: 8,
or a humanized version thereof.

The invention further comprises an antibody according to the invention, characterized in that
the heavy chain variable domain is SEQ ID NO: 15 and the light chain variable domain is SEQ ID NO: 16, or
or a humanized version thereof.

The invention further comprises an antibody according to the invention, characterized in that
the heavy chain variable domain is SEQ ID NO: 23 and the light chain variable domain is SEQ ID NO: 24, or
or a humanized version thereof.

The invention further comprises an antibody according to the invention, characterized in that
the heavy chain variable domain is SEQ ID NO: 31 and the light chain variable domain is SEQ ID NO: 32, or
or a humanized version thereof.

The invention further comprises an antibody according to the invention, characterized in that
the heavy chain variable domain comprises a CDRH1 region of SEQ ID NO: 9, a CDRH2 region of SEQ ID NO: 10, and a CDRH3 region of SEQ ID NO: 11, and the light chain variable domain comprises a CDRL1 region of SEQ ID NO: 12, a CDRL2 region of SEQ ID NO: 13, and a CDRL3 region of SEQ ID NO: 14, or The invention further comprises an antibody according to the invention, characterized in that
the heavy chain variable domain comprises a CDRH1 region of SEQ ID NO: 17, a CDRH2 region of SEQ ID NO: 18, and a CDRH3 region of SEQ ID NO: 19, and the light chain variable domain comprises a CDRL1 region of SEQ ID NO: 20, a CDRL2 region of SEQ ID NO: 21, and a CDRL3 region of SEQ ID NO: 22, or The invention further comprises an antibody according to the invention, characterized in that
the heavy chain variable domain comprises a CDRH1 region of SEQ ID NO: 25, a CDRH2 region of SEQ ID NO: 26, and a CDRH3 region of SEQ ID NO: 27, and the light chain variable domain comprises a CDRL1 region of SEQ ID NO: 28, a CDRL2 region of SEQ ID NO: 29, and a CDRL3 region of SEQ ID NO: 30.

The term "antibody" encompasses the various forms of antibody structures including but not being limited to whole antibodies and antibody fragments. The antibody according to the invention is preferably a humanized antibody, chimeric antibody, or further genetically engineered antibody as long as the characteristic properties according to the invention are retained. "Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to CDCP1, namely being able to assemble together with a $V_H$ domain to a functional antigen binding site and thereby providing the properties of an antibody according to the invention. The terms "monoclonal antibody" or "monoclonal antibody composition" as used herein refer to a preparation of antibody molecules of a single amino acid composition. The term "humanized antibody" or "humanized version of an antibody" refers to antibodies in which the framework and/or "complementary determining regions" (CDR) have been modified to comprise the CDR (e.g. CDR3) of an immunoglobulin of different species as compared to that of the parent immunoglobulin. In a preferred embodiment, a mouse CDR (e.g. CDR3) is grafted into the framework region of a human antibody to prepare the "humanized antibody" (see, e.g., Riechmann, L. et al., Nature 332 (1988) 323-327; and Neuberger, M. S. et al., Nature 314 (1985) 268-270).

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such rat/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art (see, e.g., Morrison, S. L. et al., Proc. Natl. Acad. Sci. USA 81 (1984) 6851-6855; U.S. Pat. No. 5,202,238 and U.S. Pat. No. 5,204,244).

Human CDCP1 ((CUB domain containing protein 1, B345, CD318, SIMA135, TRASK; SEQ ID NO: 1 and variants with mutation R525Q (i.e. replacement of Arginine (R) with Glutamine (Q) at amino acid position 525 of SEQ ID NO: 1) and/or mutation G709D (i.e. replacement of Glycine (G) with Aspartic acid (D) at amino acid position 709 of SEQ ID NO: 1)) is a transmembrane protein containing three extracellular CUB domains. This protein is found to be overexpressed in colon and lung cancers. Its expression level is correlated with the metastatic ability of carcinoma cells. It has been shown to be tyrosine phosphorylated in a cancer cell line. (WO 2002/004508; Scherl-Mostageer, M., et al., Oncogene 20 (2001) 4402-8; Hooper, J. D. et al., Oncogene 22 (2003) 1783-94; Perry, S. E. et al., FEBS Lett. 581 (2007) 1137-42; Brown, T. A., J. Biol. Chem. 279 (2004) 14772-14783; Ota, T. et al., Nat. Genet. 36 (2004) 40-45). Alternatively spliced transcript variants encoding distinct isoforms have been reported.

The term "Kabat numbering" or "numbering according to Kabat" or "EU index" unless otherwise stated, is defined as the numbering of the residues in, e.g., an IgG antibody using the EU index as in Kabat, et al. (Sequences of Proteins of Immunological Interest, 5th ed., Public Health Service, National Institutes of Health, Bethesda, Md. (1991)).

As used herein, "specifically binding to human CDCP1" refers to an antibody specifically binding to the human CDCP1 antigen. The binding affinity is of KD-value of $1.0 \times 10^{-8}$ mol/l or lower, preferably of a KD-value of $1.0 \times 10^{-9}$ mol/l or lower. The binding affinity is determined with a standard binding assay, such as surface plasmon resonance technique (Biacore®). Thus an "antibody specifically binding to human CDCP1" as used herein refers to an antibody binding to human CDCP1 antigen with a binding affinity of KD $1.0 \times 10^{-8}$ mol/l or lower (e.g. of KD $1.0 \times 10^{-8}$ mol/l-$1.0 \times 10^{-13}$ mol/l, preferably of KD $1.0 \times 10^{-9}$ mol/l-$1.0 \times 10^{-12}$ mol/l).

The invention further comprises an antibody specifically binding to human CDCP1, characterized in that
   the heavy chain variable domain is SEQ ID NO: 15 and the light chain variable domain is SEQ ID NO: 16, or a humanized version thereof.

The invention further comprises an antibody specifically binding to human CDCP1, characterized in that
   the heavy chain variable domain is SEQ ID NO: 23 and the light chain variable domain is SEQ ID NO: 24, or a humanized version thereof.

The invention further comprises an antibody specifically binding to human CDCP1, characterized in that
   the heavy chain variable domain is SEQ ID NO: 31 and the light chain variable domain is SEQ ID NO: 32, or a humanized version thereof.

The invention further comprises an antibody specifically binding to human CDCP1, characterized in that
   the heavy chain variable domain comprises a CDRH1 region of SEQ ID NO: 9, a CDRH2 region of SEQ ID NO: 10, and a CDRH3 region of SEQ ID NO: 11, and the light chain variable domain comprises a CDRL1 region of SEQ ID NO: 12, a CDRL2 region of SEQ ID NO: 13, and a CDRL3 region of SEQ ID NO: 14.

The invention further comprises an antibody specifically binding to human CDCP1, characterized in that
   the heavy chain variable domain comprises a CDRH1 region of SEQ ID NO: 17, a CDRH2 region of SEQ ID NO: 18, and a CDRH3 region of SEQ ID NO: 19, and the light chain variable domain comprises a CDRL1 region of SEQ ID NO: 20, a CDRL2 region of SEQ ID NO: 21, and a CDRL3 region of SEQ ID NO: 22.

The invention further comprises an antibody specifically binding to human CDCP1, characterized in that
   the heavy chain variable domain comprises a CDRH1 region of SEQ ID NO: 25, a CDRH2 region of SEQ ID NO: 26, and a CDRH3 region of SEQ ID NO: 27, and the light chain variable domain comprises a CDRL1 region of SEQ ID NO: 28, a CDRL2 region of SEQ ID NO: 29, and a CDRL3 region of SEQ ID NO: 30.

The term "epitope" denotes a protein determinant of human CDCP1 capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents.

Figure 2:
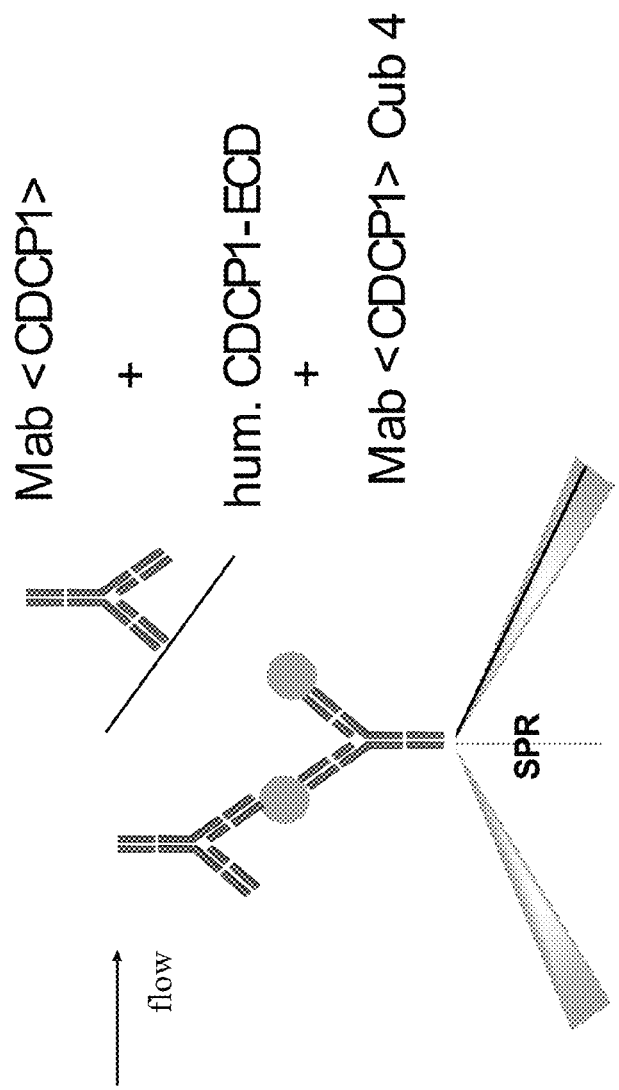
FIG. 2 Schematic Assay format of Surface Plasmon Resonance (SPR-)technology (BIAcore®) with immobilized CUB4 antibody, extracellular domain (ECD) of CDCP1, and further anti-CDCP1 test antibodies (e.g. CUB1 and CUB3).

The term "binding to the same epitope as CUB4 (Deposition No. DSM ACC2551)" as used herein refers to an anti-CDCP1 antibody of the invention that binds to the same epitope on CDCP1 to which the antibody CUB4 (Deposition No. DSM ACC2551) binds. The epitope binding property of an anti-CDCP1 antibody of the present invention may be determined using techniques known in the art. The CDCP1 antibody is measured at 25° C. by Surface Plasmon Resonance (SPR) in an in vitro competitive binding inhibition assay to determine the ability of antibody CUB4 (Deposition No. DSM ACC2551) to inhibit binding of the test antibody to CDCP1 (see FIG. 2). Binding of antibodies binding to the same epitope as CUB4 is inhibited and no binding signal is detected after addition of the test antibody. (e.g. 100 seconds after the injection time (=0 seconds) of the test antibody the binding signal is not higher than the signal at the time of injection; the signal is measured in RU (Relative Units)) (e.g. CDCP1-004, CDCP1-012, CDCP1-015, see FIG. 3a). Binding of antibodies binding to a different epitope as CUB4 is not inhibited and a binding signal is detected after addition of the test antibody (e.g. CUB1 and CUB3, see FIG. 3b) (e.g. 100 seconds after the injection time (=0 seconds) the binding signal is higher than the signal at the time of injection; the signal is measured in RU (Relative Units)). This can be investigated by a BIAcore assay (Pharmacia Biosensor AB, Uppsala, Sweden) as described. e.g. in Example 2.

The "variable domain" (variable domain of a light chain (VL), variable domain of a heavy chain (VH)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". The term "antigen-binding portion" of an antibody of the invention may contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

"Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The antibody according to the invention is characterized in that the constant region is of human origin, and is preferably of human IgG1 subclass. The constant region includes the heavy chain and light chain constant region of an antibody. The heavy chain constant region comprises in N-terminal to C-terminal direction an antibody constant heavy chain domain 1 (CH1), an antibody hinge region (HR), an antibody heavy chain constant domain 2 (CH2), and an antibody heavy chain constant domain 3 (CH3), and optionally an antibody heavy chain constant domain 4 (CH4) in case of an antibody of the subclass IgE. The light chain constant region comprises an antibody light chain constant domain (CL). The antibody light chain constant domain (CL) can be κ (kappa) or λ (lambda). Such constant chains are well known in the state of the art and e.g. described by Kabat, E., A., (see e.g. Johnson, G. and Wu, T., T., Nucleic Acids Res. 28 (2000) 214-218). For example, a useful human heavy chain constant region of IgG1 subclass comprises an amino acid sequence of SEQ ID NO: 3. For example, a useful human light chain constant region comprises an amino acid sequence of a kappa-light chain constant region of SEQ ID NO: 4; another useful human light chain constant region comprises an amino acid sequence of a lambda-light chain constant region of SEQ ID NO: 5.

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ respectively.

The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J. et al., Nature 282 (1979) 742-743; Lukas, T. J. et al., J. Immunol. 127 (1981) 2555-2560; Brunhouse, R. and Cebra, J. J., Mol. Immunol. 16 (1979) 907-917; Burton, D. R. et al., Nature 288 (1980) 338-344; Thommesen, J. E. et al., Mol. Immunol. 37 (2000) 995-1004; Idusogie, E. E. et al., J. Immunol. 164 (2000) 4178-4184; Hezareh, M. et al., J. Virology 75 (2001) 12161-12168; Morgan, A. et al., Immunology 86 (1995) 319-324; EP 0307434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

The antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P). Mostly preferred are the human heavy chain constant regions of human IgG1 subclass (see e.g. of SEQ ID NO: 3), of human IgG1 subclass with mutations L234A and L235A, of human IgG4 subclass (see e.g. of SEQ ID NO: 6), or of human IgG4 subclass with mutation S228P.

The term "antibody-dependent cellular cytotoxicity (ADCC)" refers to lysis of human target cells by an antibody according to the invention in the presence of effector cells. ADCC is measured preferably by the treatment of a preparation of CDCP1 expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

Cell-mediated effector functions of monoclonal antibodies can be enhanced by engineering their oligosaccharide component as described in Umana, P. et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R. et al., Glycobiology 5 (1995) 813-822; Jefferis, R. et al., Immunol. Rev. 163 (1998) 59-76; Wright, A. and Morrison, S. L., Trends Biotechnol. 15 (1997) 26-32). Umana, P., et al. Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P. et al., Nature Biotechnol. 17 (1999) 176-180; Davies, J. et al., Biotechnol. Bioeng. 74 (2001) 288-294; Mimura, Y. et al., J. Biol. Chem. 276 (2001) 45539-45547; Radaev, S. et al., J. Biol. Chem. 276 (2001) 16478-16483; Shields, R. L. et al., J. Biol. Chem. 276 (2001) 6591-6604; Shields, R. L. et al., J. Biol. Chem. 277 (2002) 26733-26740; Simmons, L. C. et al., J. Immunol. Methods 263 (2002) 133-147).

Methods to enhance cell-mediated effector functions of monoclonal antibodies are reported e.g. in WO 2005/044859, WO 2004/065540, WO2007/031875, Umana, P. et al., Nature Biotechnol. 17 (1999) 176-180, WO 99/154342, WO 2005/018572, WO 2006/116260, WO 2006/114700, WO 2004/065540, WO 2005/011735, WO 2005/027966, WO 1997/028267, WO 2006/0134709, US 2005/0054048, US 2005/0152894, WO 2003/035835 and WO 2000/061739 or e.g. in Niwa, R. et al., J. Immunol. Methods 306 (2005) 151-160; Shinkawa, T. et al., J. Biol. Chem. 278 (2003) 3466-3473; WO 03/055993 and US 2005/0249722.

Therefore in one embodiment of the invention, the antibody according to the invention is glycosylated (if it comprises an Fc part of IgG1 or IgG3 subclass) with a sugar chain at Asn297 whereby the amount of fucose within said sugar chain is 65% or lower (Numbering according to Kabat). In another embodiment is the amount of fucose within said sugar chain is between 5% and 65%, preferably between 20% and 40%. "Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300. In one embodiment the glycosylated antibody according to the invention the IgG subclass is of human IgG1 subclass, of human IgG1 subclass with the mutations L234A and L235A or of IgG3 subclass. In a further embodiment the amount of N-glycolylneuraminic acid (NGNA) is 1% or less and/or the amount of N-terminal alpha-1,3-galactose is 1% or less within said sugar chain. The sugar chains show preferably the characteristics of N-linked glycans attached to Asn297 of an antibody recombinantly expressed in a CHO cell.

The term "the sugar chains show characteristics of N-linked glycans attached to Asn297 of an antibody recombinantly expressed in a CHO cell" denotes that the sugar chain at Asn297 of the antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E. A., et al., Sequences of Proteins of Immunological Interest, 5th ed., Public Health Service, National Institutes of Health, Bethesda, Md. (1991), and by Brueggemann, M., et al., J. Exp. Med. 166 (1987) 1351-1361; Love, T. W. et al., Methods Enzymol. 178 (1989) 515-527. These structures are designated as G0, G1 (α-1,6- or α1,3-), or G2 glycan residues, depending from the amount of terminal Gal residues (Raju, T. S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by MALDI-TOF mass spectrometry and calculated as average value (see e.g. WO 2008/077546). The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or E. coli cells, and the antibody is recovered from the cells (supernatant or cells after lysis).

Recombinant production of antibodies is well-known in the state of the art and described, for example, in the review articles of Makrides, S. C., Protein Expr. Purif. 17 (1999) 183-202; Geisse, S. et al., Protein Expr. Purif. 8 (1996) 271-282; Kaufman, R. J., Mol. Biotechnol. 16 (2000) 151-160; Werner, R. G., Drug Res. 48 (1998) 870-880.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art (see Ausubel, F., et al., ed. Current Protocols in Molecular Biology, Greene Publishing and Wiley Interscience, New York (1987).

Expression in NS0 cells is described by, e.g., Barnes, L. M. et al., Cytotechnology 32 (2000) 109-123; and Barnes, L. M. et al., Biotech. Bioeng. 73 (2001) 261-270. Transient expression is described by, e.g., Durocher, Y. et al., Nucl. Acids. Res. 30 (2002) E9. Cloning of variable domains is described by Orlandi, R. et al., Proc. Natl. Acad. Sci. USA 86 (1989) 3833-3837; Carter, P. et al., Proc. Natl. Acad. Sci. USA 89 (1992) 4285-4289; and Norderhaug, L. et al., J. Immunol. Methods 204 (1997) 77-87. A preferred transient expression system (HEK 293) is described by Schlaeger, E. J., and Christensen, K., in Cytotechnology 30 (1999) 71-83 and by Schlaeger, E. J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L. and van der Eb, A. J., Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S. N. et al., PNAS 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antigen binding protein according to the present invention, formulated together with a pharmaceutical carrier.

Said antibodies specifically binding to human CDCP1 characterized in binding to same epitope as CUB4 (Deposition No. DSM ACC2551) have been turned out to be especially useful for the treatment of cancer compared with other anti-CDCP1 antibodies as e.g. CUB1 antibody (deposited antibody with the Deposition No. DSM ACC2569 from DE 10242146 (EP 1 396 501, U.S. Pat. No. 7,541,030)).

Therefore one aspect of the invention is said pharmaceutical composition for the treatment of cancer.

Another aspect of the invention is the use of an antibody according to the invention for the manufacture of a medicament for the treatment of cancer.

Another aspect of the invention is a method of treatment of a patient suffering from cancer by administering an antibody according to the invention to said patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, ovarian cancer, cervical cancer, lung cancer or prostate cancer and more preferably lung cancer. Preferably such cancers are further characterized by CDCP1 expression or overexpression. More preferably such cancers are further characterized by overexpression.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO:1 human CDCP1
SEQ ID NO:2 extracellular-domain-(ECD)-comprising fragment of human CDCP1):
SEQ ID NO:3 IgG1 constant heavy chain region from human origin
SEQ ID NO:4 kappa constant light chain region from human origin
SEQ ID NO:5 lambda constant light chain region from human origin
SEQ ID NO:6 IgG4 constant heavy chain region from human origin SEQ ID NO: 7 heavy chain variable domain VH, CUB4 (Deposition No. DSM ACC2551)
SEQ ID NO: 8 light chain variable domain VL, CUB4 (Deposition No. DSM ACC2551)
SEQ ID NO: 9 heavy chain CDRH1, Mab CDCP1-004
SEQ ID NO: 10 heavy chain CDRH2, Mab CDCP1-004
SEQ ID NO: 11 heavy chain CDRH3, Mab CDCP1-004
SEQ ID NO: 12 light chain CDRL1, Mab CDCP1-004
SEQ ID NO: 13 light chain CDRL2, Mab CDCP1-004
SEQ ID NO: 14 light chain CDRL3, Mab CDCP1-004
SEQ ID NO: 15 heavy chain variable domain VH, Mab CDCP1-004
SEQ ID NO: 16 light chain variable domain VL, Mab CDCP1-004
SEQ ID NO: 17 heavy chain CDRH1, Mab CDCP1-012
SEQ ID NO: 18 heavy chain CDRH2, Mab CDCP1-012
SEQ ID NO: 19 heavy chain CDRH3, Mab CDCP1-012
SEQ ID NO: 20 light chain CDRL1, Mab CDCP1-012
SEQ ID NO: 21 light chain CDRL2, Mab CDCP1-012
SEQ ID NO: 22 light chain CDRL3, Mab CDCP1-012
SEQ ID NO: 23 heavy chain variable domain VH, Mab CDCP1-012
SEQ ID NO: 24 light chain variable domain VL, Mab CDCP1-012
SEQ ID NO: 25 heavy chain CDRH1, Mab CDCP1-015
SEQ ID NO: 26 heavy chain CDRH2, Mab CDCP1-015
SEQ ID NO: 27 heavy chain CDRH3, Mab CDCP1-015
SEQ ID NO: 28 light chain CDRL1, Mab CDCP1-01510
SEQ ID NO: 29 light chain CDRL2, Mab CDCP1-015
SEQ ID NO: 30 light chain CDRL3, Mab CDCP1-015
SEQ ID NO: 31 heavy chain variable domain VH, Mab CDCP1-015
SEQ ID NO: 32 light chain variable domain VL, Mab CDCP1-015

Example 1

In Vivo Tumor Growth Inhibition of Anti-CDCP1 Antibody CUB4 and in Comparison to CUB1 Antibody Study name: CDCP1_PZ_H322M_002

The present in vivo study was be performed to compare the efficacy of anti-CDCP1 specific antibodies CUB4 with antibodies binding another epitope, as e.g. CUB1

H322M non small cell lung cancer cells were originally obtained from the NCI collection and were deposited after expansion in the Roche cell bank, Penzberg. Tumor cell line was routinely cultured in RPMI 1640 medium supplemented with 10% fetal bovine serum and 2 mM L-glutamine at 37° C. in a water-saturated atmosphere at 5% CO2. Passage 4 was used for cell transplantation.

The human non small cell lung cancer cell line H322M was subcutaneously inoculated ($5\times10^6$ cells) with matrigel into the right flank of the mice.

Animal treatment started at the day of randomisation 17 days after cell transplantation. Antibodies were administered i.p. q7d until study termination day 62 at the indicated dosage of 10 mg/kg. Also the corresponding vehicle was administered on the same days. The administration volume was 10 ml/kg.

Groups:
Treatment Group 1: Vehicle
Treatment Group 2: murine CUB4 10 mg/kg i.p.;
Treatment Group 3: murine CUB1 10 mg/kg i.p.;
TGI (Tumor Growth Inhibition in %)

The following tables show the values of the tumor growth inhibition, which is calculated as 100−Average(T_treatment[day x]−T_treatment[baseline])/Average(T_reference[day x]−T_reference[baseline])*100 for each group and time point based on means and medians, respectively. The reference for the TGI calculations was chosen to be group 'Vehicle'. Results are also shown in FIG. 1.

TABLE 1

Tumor growth inhibition (TGI)

| Group | Compound | Treatment schedule | Dose (mg/kg) | Median tumor volume at staging day 17 ($mm^3$) | Median tumor volume at day 62, ($mm^3$) | TGI % |
|---|---|---|---|---|---|---|
| 1 | vehicle | 1x/week i.p. | — | 175.7 | 926.3 | — |
| 2 | CUB4 | 1x/week i.p. | 10 mg/kg | 174.7 | 311.8 | 82 |
| 3 | CUB1 | 1x/week i.p. | 10 mg/kg | 172.8 | 414.1 | 68 |

The CUB4 antibody (Deposition No. DSM ACC2551) surprisingly shows a clearly higher tumor growth inhibition than CUB1 antibody (deposited antibody with the Deposition No. DSM ACC2569 from DE 10242146 (EP 1 396 501, U.S. Pat. No. 7,541,030)).

Analogously the in vivo tumor growth inhibition of the anti-CDCP1 antibodies according to the invention CDCP1 004, CDCP1 012 and CDCP1 015 can be determined.

Example 2

Epitope Binding Assay (Biacore)

To determine the epitope regions of different test anti-CDCP1 antibodies, CUB4 (Deposition No. DSM ACC2551) was immobilized on the surface of a CM5 biosensorchip using amine-coupling chemistry. Flow cells were activated with a 1:1 mixture of 0.1 M N-hydroxysuccinimide and 0.4 M 1-ethyl-3-(3-dimethylaminopropyl)carbodiimide at a flow rate of 5 μl/min. Anti-CDCP1 antibodies CUB4 (Deposition No. DSM ACC2551) was injected in sodium acetate, pH 4.5-5.0 at 10-30 μg/ml, 12 minutes, which resulted in a surface density of approx 15000 RU. Surfaces were blocked with an injection of 1 M ethanolamine/HCl pH 8.5. Soluble ECD of human CDCP1 (SEQ. ID NO.:2) (analyte 1) and anti-CDCP1 antibodies (analyte 2) were diluted in PBST+0.8M NaCl and injected at a flow rate of 30 μl/min. The contact time (association phase) was 150-200 sec for the ECD of human CDCP1 at a concentration of 250 nM-500 nM and 300 sec for the anti-CDCP1 antibody at a concentration of 100 nM. Then the chip surface was washed with PBST+0.8M NaCl for 3 min (dissociation phase). All interactions were performed at exactly 25° C. (standard temperature). A regeneration solution of 10 mM Glycine, pH 2.0 was injected for 60-150 sec to remove any non-covalently bound protein after each binding cycle. Signals were detected at a detection rate of one signal per second.

To determine whether an anti-CDCP1 antibody binds to the same or a different epitope of human CDCP1 as CUB4, the ECD of human CDCP1 was injected and bound by the immobilized antibodies. Shortly after the binding, antibodies with unknown epitope were injected. Test anti-CDCP1-antibodies which do not show an increase of the binding signal after injection (i.e. e.g. 100 seconds after the injection time (=0 seconds) of the test antibody, the binding signal is not higher than the signal at the time of injection; the signal is measured in RU (Relative Units)), are binding to the same epitope as CUB4. Test anti-CDCP1-antibodies which show an increase of the binding signal are binding to a different epitope as CUB4 (e.g. 100 seconds after the injection time (=0 seconds) the binding signal is higher than the signal at the time of injection; the signal is measured in RU (Relative Units)).

Figure 3B:
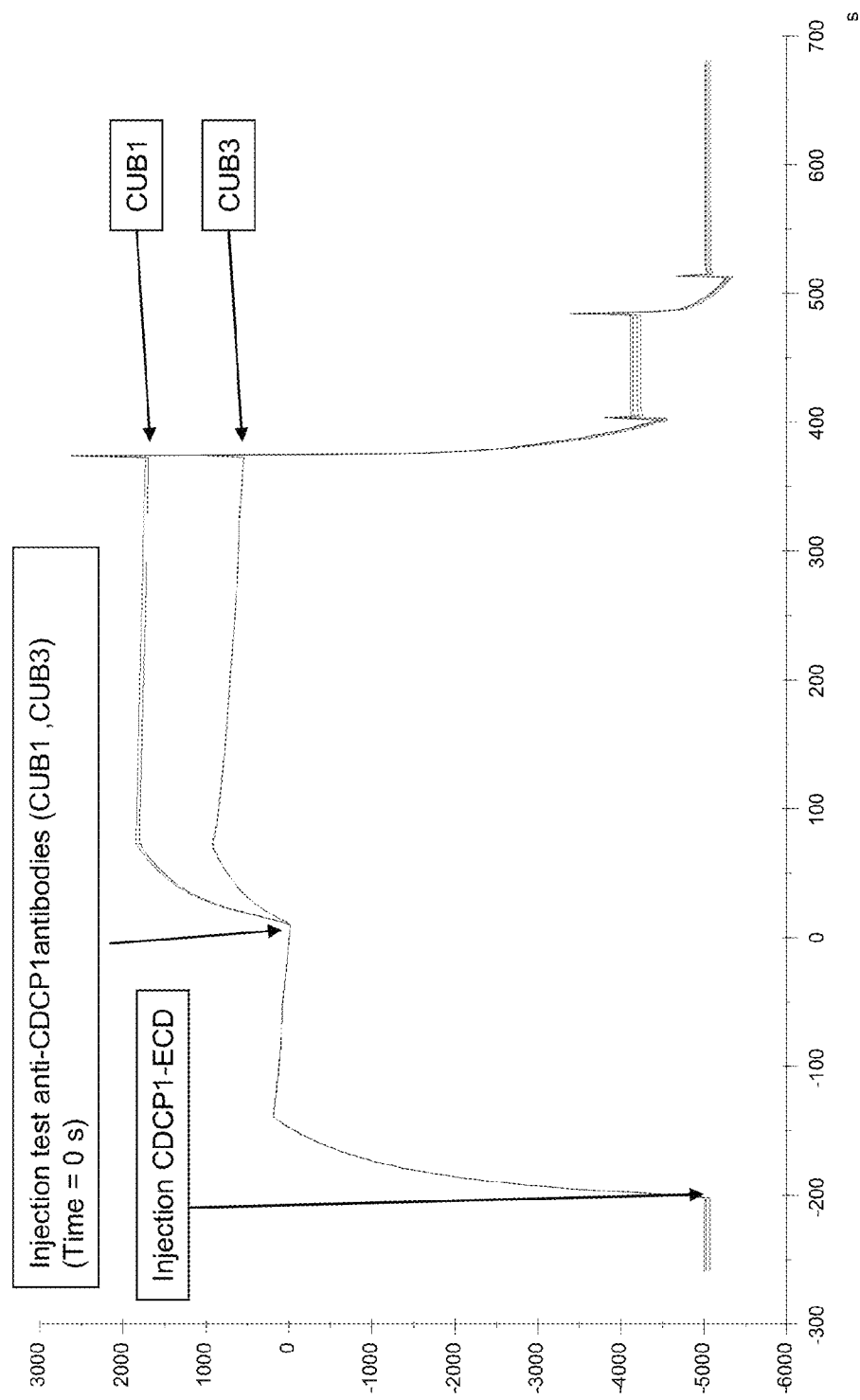
FIG. 3b: The binding of CUB1 and CUB3 antibodies to another epitope on CDCP1 than CUB4 antibody is shown.

Results of the triple determinations are shown in FIG. 3 a and 3 b. Antibodies CUB3, CUB1 (see FIG. 3b) were found to bind at different epitopes as CUB4, whereas anti-CDCP1 antibodies CDCP1-004, CDCP1-012 and CDCP1-015 were identified as binding to the same epitope as CUB4 (see Table 2 and FIG. 3a, all triple experiments). Antibodies CUB3 and CUB1 each were found to bind to another epitope as CUB4 and are different from one another (CUB1 CUB3). (see Table 2 and FIG. 3b, all triple experiments). Control experiments with CUB4 and dilution buffer as negative controls did not show an increase in the binding signal.

CUB1 showed no sandwich complex formation with preformed complex consisting of amine coupled Mab CUB3 and vice versa. (data not shown).

CDCP1-004, CDCP1-012 and CDCP1-015 showed a sandwich complex formation with both preformed complexes consisting of Mab CUB1 or Mab CUB3, respectively and antigene. (data not shown)

TABLE 2

(see also FIG. 3):

| Antibodies binding to the same epitope as CUB4 | Antibodies binding to the different epitope as CUB4 |
| --- | --- |
| Murine CUB4<br>Chimeric CUB4<br>Murine CDCP1-004<br>Murine CDCP1-012<br>Murine CDCP1-015 | Murine CUB1<br>Murine CUB3 |

In a separate Biacore experiment the binding constants and affinities of anti-CDCP1 antibodies to immobilized hCDCP1-ECD have been determined as follows:

TABLE 3

| Mab <hCDCP1> | antigene | $k_a$ [1/Ms] | $k_d$ [1/s] | $K_D$[M] | t(½) [min] |
| --- | --- | --- | --- | --- | --- |
| Mab CUB4 | hum. CDCP1 ECD | 9.9E+05 | 5.2E−04 | 5.2E−10 | 22.4 |
| Mab CDCP1-015 | hum. CDCP1 ECD | 4.6E+05 | 2.2E−04 | 4.7E−10 | 52.8 |
| Mab CUB1 | hum. CDCP1 ECD | 1.4E+06 | 1.9E−02 | 1.4E−08 | 0.6 |
| Mab CUB3 | hum. CDCP1 ECD | 5.4E+04 | 3.1E−02 | 5.7E−07 | 0.4 |

$k_a$: association rate constant, $k_d$ dissociation rate constant, $K_D$ dissociation equilibrium constant (binding affinity), t½: halflife time of complex, Example 3

Antigene Specific ELISA

Soluble CDCP1 extracellular Domain (CDCP1-ECD) (SEQ ID No: 2), as well as Short1 (huCDCP1_SH1_ECD aa1-216)_SBP) and Short5 (hu CDCP1_SH5_ECD (aa 1-361)_SBP), which comprehend amino acids 1-216 of CDCP1 extracellular domain and 1-361 of CDCP1 extracellular domain, respectively, each fused to streptavidine Binding Protein (SBP) (SEQ ID No: 2), were captured on a streptavidine plate. To define optimal binding of the antibodies to SBP-CDCP1-ECD, SBP-CDCP1 Short1 and SBP-CDCP1-Short5, 96 well polystyrene plates (Roche, streptavidin-coated, ID-No. 1989685) have been coated with pure or 1:4 diluted (dissolved in Dulbecco's Modified Eagle's Medium, PAN Biotech, containing 10% of Fetal Bovine Serum, Pan Biotech ID-No 3302-P251116) HEK293 supernatant. For the standard coating, SBP-CDCP1-Short5 containing HEK293 supernatant was diluted (1:4) contrary to undiluted SBP-CDCP1-Short1 and SBP-CDCP1-ECD supernatant and incubated overnight at 2-8° C. (60 µl). Intensive washing of the microtiter plate is necessary to remove remaining unbound SBP-CDCP1-ECD, SBP-CDCP1-Short1 and SBP-CDCP1-Short5.

The coated wells were blocked by performing an one hour blocking step using blocking reagent for ELISA (Roche 11112589) 250 µl/well.

Anti-CDCP1 antibodies CUB4 (Deposition No. DSM ACC2551) and CDCP1 004, CDCP1 012 and CDCP1 015 were tested using a 1:500 dilution (0.1 µg antibody diluted in 50 µl PBS containing 1% BSA Fraction V, Sigma A3059). 50 µl per well for each sample was incubated for 60 minutes at room temperature. After intensive washing using PBS-T (0.05% Tween 20 in PBS, Fluka #08057) 50 µl of goat anti-mouse IgG antibodies coupled with HRP (BioRad #1706516, dilution 1:1000) were added and incubated for 1 hour at room temperature. After intensive washing the binding of the antibodies was detected with BM Blue POD Substrate (Roche 11484281001) 50 µl. Absorbance at 370 nm/492 nm was measured using a standard photometer.

Figure 4:
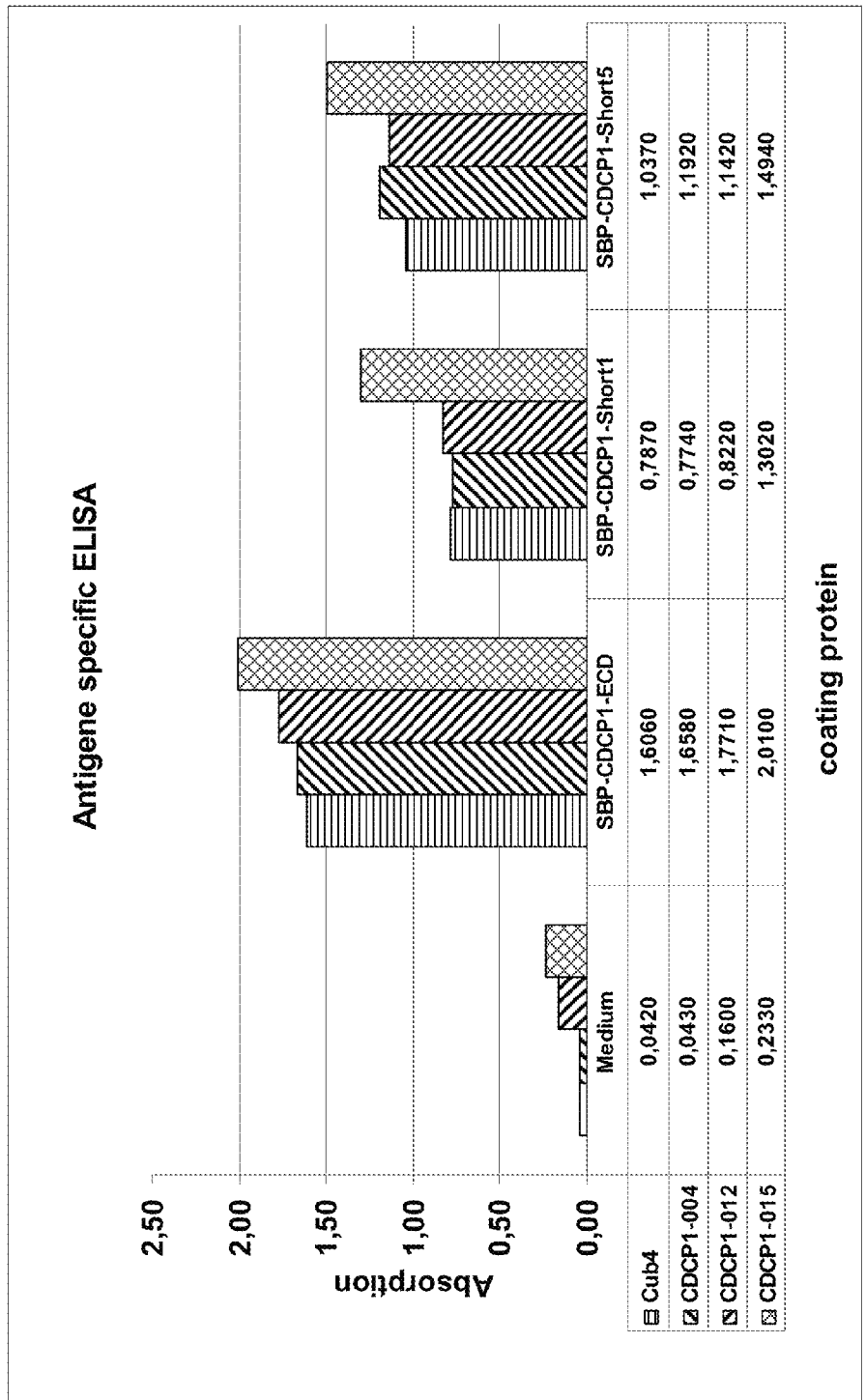
FIG. 4 Binding of the CDCP1 antibodies according to the invention to human CDCP1 Extracellular Domain (CDCP1-ECD) and subdomains of human CDCP1-ECD FIG. 5 Stimulation of CDCP1 phosphorylation in HCT 116 cells FIG. 6 Stimulation of CDCP1 internalisation and phosphorylation in MDAMB-231 cells

The binding region of the antibodies CDCP1-004, CDCP1-012, CDCP1-015 and CUB4 is located within the aa 1 and 216 in the extracellular domain of CDCP1. As a consequence all these antibodies also recognize the complete ECD of CDCP1 and a construct containing aa 1-361 (short 5) (see FIG. 4).

Example 4

Stimulation of CDCP1 Internalisation and Phosphorylation in MDAMB-231 or HCT 116 Cells $7×10^5$ per 6 well MDAMB-231 cells were cultured in DMEM+L-Glutamine, +Pyruvat (Gibco, 41966) 10% FCS (PAN Biotech ID-No 3302-P251116) 1% MEM Non Essentials Amino Acids (PAA, P0832100) over night. MDA-MB-231 cells were treated with 10 µg/of the different antibodies for 10 minutes and 5 hours: mouse CUB4 (Deposition No. DSM ACC2551) and antibodies CDCP1_004, CDCP1_012 and CDCP1 015. HCT 116 cells were treated with 20 µg/of the different antibodies for 10 minutes and 5 hours: mouse CUB4 (Deposition No. DSM ACC2551), mouse CUB1 and mouse CUB3. Cells were lysed with ice cooled freshly prepared RIPA-Lysis buffer (Thermo Scientific, #89901) containing 1 mM PMSF in Ethanol, 10 µg/ml Aprotinin, 0.4 mM Orthovanadat). After 15 minutes on ice cell lysates were centrifuged 20 minutes at 13000 rpm. The lysates were separated on SDS-PAGE by standard protocol and transferred to nitrocellulose by Western blotting. Western Blots were detected by an anti-CDCP1 antibody (cell signaling #4115), an anti-phospho-CDCP1 antibody or PY 4G10 in the case of HCT116.

Figure 5A:
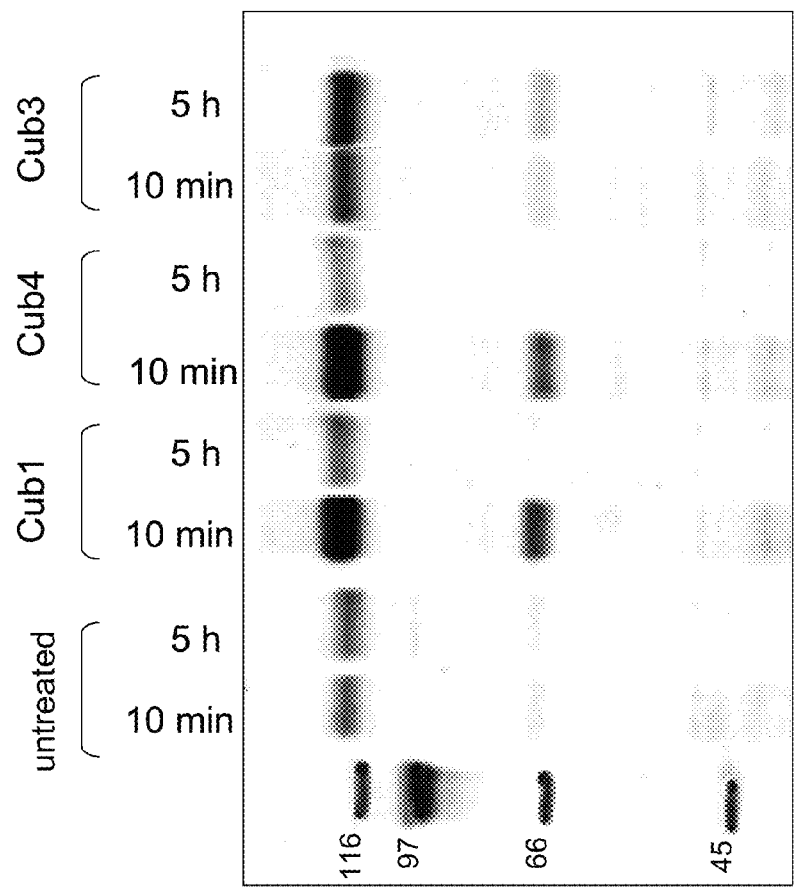

Phosphorylation level of CDCP1 present in untreated HCT116 cells is unchanged at time point 10 minutes or 5 hours. CUB4 mediates a stronger phosphorylation of CDCP1 after 10 min incubation of the cell compared to CUB1. Inhibition of phosphorylation and down modulation (data not shown) of CDCP1 is much more pronounced by CUB4 compared to CUB1. CUB3 incubation leads to weak stimulation of CDCP1 phosphorylation and can not mediated down-modulation (data not shown) of the protein. Results are shown in FIGS. 5a and b.

Figure 6A:
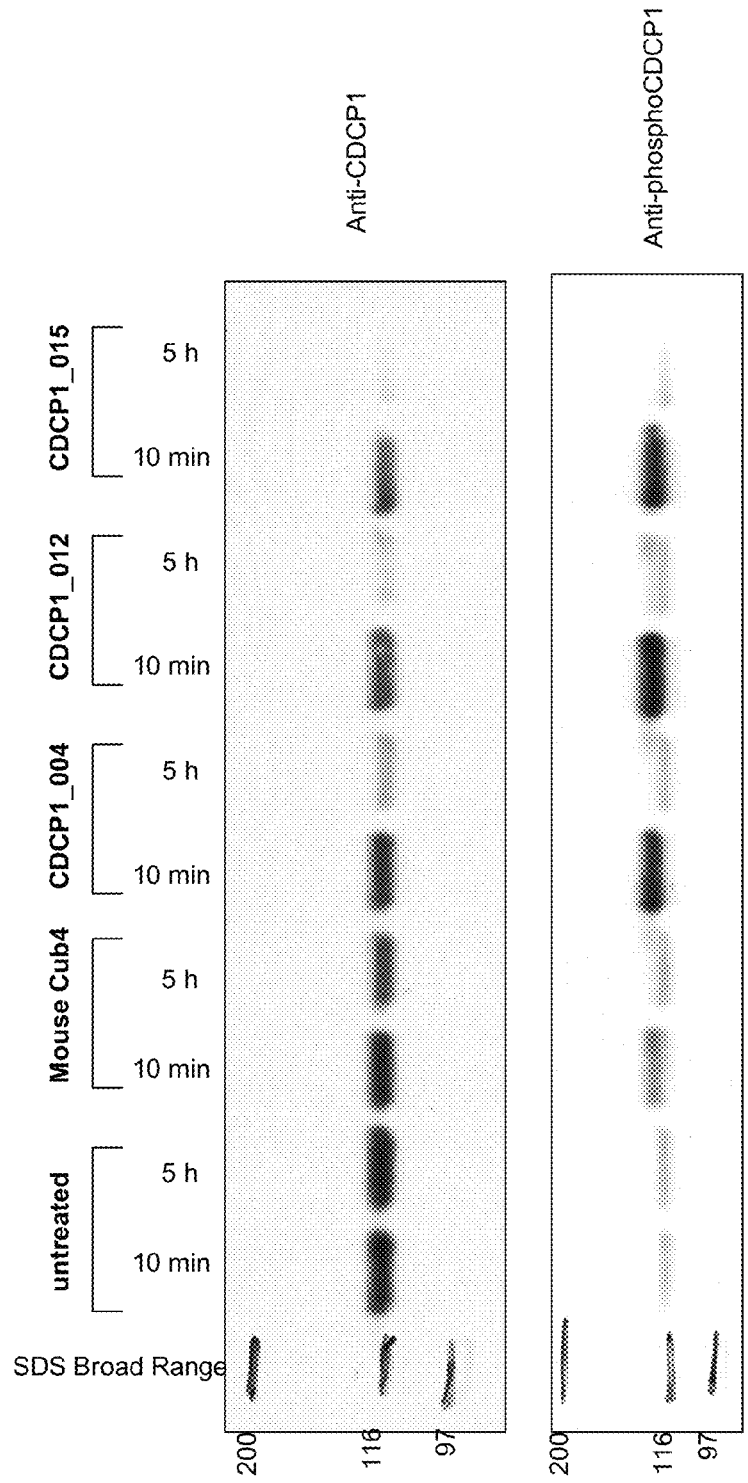

Expression level of CDCP1 present in untreated MDA-MB231 cells is unchanged at time point 10 minutes or 5 hours. CUB4 incubation as well as incubation of the cells with CDCP1-004, CDCP1-012 and CDCP1-0015 antibody for 5 hours leads at least to partial degradation of the CDCP1 protein. Phosphorylation of CDCP1 is hard to detect in the untreated cell. Treatment of cells for 10 min with CUB4 or the antibodies CDCP1-004, CDCP1-012 and CDCP1-0015 leads to an increase of CDCP1 phosphorylation on tyrosine 734. After 5 hour treatment with these antibodies as a consequence of the CDCP1 down modulation the phosphorylation of tyrosine 734 in CDCP1 barely to detect. Results are shown in FIG. 6a to c.

What is claimed is:

1. An isolated antibody that specifically binds to human CDCP1, characterized in that (a) the heavy chain variable domain comprises a CDRH1 region of SEQ ID NO:9, a CDRH2 region of SEQ ID NO:10, and a CDRH3 region of SEQ ID NO:11, and the light chain variable domain comprises a CDRL1 region of SEQ ID NO:12, a CDRL2 region of SEQ ID NO:13, and a CDRL3 region of SEQ ID NO:14, or (b) the heavy chain variable domain comprises a CDRH1 region of SEQ ID NO:17, a CDRH2 region of SEQ ID NO:18, and a CDRH3 region of SEQ ID NO:19, and the light chain variable domain comprises a CDRL1 region of SEQ ID NO:20, a CDRL2 region of SEQ ID NO:21, and a CDRL3 region of SEQ ID NO:22, or (c) the heavy chain variable domain comprises a CDRH1 region of SEQ ID NO:25, a CDRH2 region of SEQ ID NO:26, and a CDRH3 region of SEQ ID NO:27, and the light chain variable domain comprises a CDRL1 region of SEQ ID NO:28, a CDRL2 region of SEQ ID NO:29, and a CDRL3 region of SEQ ID NO:30, or (d) a humanized version of (a), (b) or (c), wherein the isolated antibody shows more than 50% internalization after 5 hours in MDAMB-231 cells as compared to an untreated control.

2. The antibody according to claim 1, characterized in that (a) the heavy chain variable domain is SEQ ID NO:15 and the light chain variable domain is SEQ ID NO:16, or (b) the heavy chain variable domain is SEQ ID NO:23 and the light chain variable domain is SEQ ID NO:24, or (c) the heavy chain variable domain is SEQ ID NO:31 and the light chain variable domain is SEQ ID NO:32, or (d) a humanized version of (a), (b), or (c).

3. The antibody according to claim 2, characterized in that the heavy chain variable domain is SEQ ID NO:15 and the light chain variable domain is SEQ ID NO:16.

4. The antibody according to claim 2, characterized in that the heavy chain variable domain is SEQ ID NO:23 and the light chain variable domain is SEQ ID NO:24.

5. The antibody according to claim 2, characterized in that the heavy chain variable domain is SEQ ID NO:31 and the light chain variable domain is SEQ ID NO:32.

6. The antibody according to claim 1, characterized in that the heavy chain variable domain comprises a CDRH1 region of SEQ ID NO:9, a CDRH2 region of SEQ ID NO:10, and a CDRH3 region of SEQ ID NO:11, and the light chain variable domain comprises a CDRL1 region of SEQ ID NO:12, a CDRL2 region of SEQ ID NO:13, and a CDRL3 region of SEQ ID NO:14.

7. The antibody according to claim 1, characterized in that the heavy chain variable domain comprises a CDRH1 region of SEQ ID NO:17, a CDRH2 region of SEQ ID NO:18, and a CDRH3 region of SEQ ID NO:19, and the light chain variable domain comprises a CDRL1 region of SEQ ID NO:20, a CDRL2 region of SEQ ID NO:21, and a CDRL3 region of SEQ ID NO:22.

8. The antibody according to claim 1, characterized in that the heavy chain variable domain comprises a CDRH1 region of SEQ ID NO:25, a CDRH2 region of SEQ ID NO:26, and a CDRH3 region of SEQ ID NO:27, and the light chain variable domain comprises a CDRL1 region of SEQ ID NO:28, a CDRL2 region of SEQ ID NO:29, and a CDRL3 region of SEQ ID NO:30.

9. The antibody according to claim 1, characterized in that said antibody is of human IgG1 subclass.

10. A pharmaceutical composition comprising the antibody of claim 1.

* * * * *